(12) United States Patent
Kriesel et al.

(10) Patent No.: US 8,057,435 B2
(45) Date of Patent: *Nov. 15, 2011

(54) FLUID DISPENSER

(76) Inventors: Joshua W. Kriesel, San Francisco, CA (US); Marshall S. Kriesel, Saint Paul, MN (US); Thomas N. Thompson, Richfield, MN (US)

(*) Notice: Subject to any disclaimer, the term of this patent is extended or adjusted under 35 U.S.C. 154(b) by 146 days.

This patent is subject to a terminal disclaimer.

(21) Appl. No.: 11/888,735

(22) Filed: Jul. 31, 2007

(65) Prior Publication Data

US 2008/0027386 A1 Jan. 31, 2008

Related U.S. Application Data

(60) Provisional application No. 60/834,770, filed on Jul. 31, 2006.

(51) Int. Cl.
*A61M 37/00* (2006.01)
*A61M 5/20* (2006.01)

(52) U.S. Cl. .................. 604/132; 604/134; 604/139

(58) Field of Classification Search .......... 604/131, 604/132–139, 151, 153, 156, 157, 212, 216, 604/207, 246, 256
See application file for complete search history.

(56) References Cited

U.S. PATENT DOCUMENTS

| | | | |
|---|---|---|---|
| 2,236,084 A | 3/1941 | Brown | |
| RE27,155 E | 7/1971 | Hansen | |
| 3,731,681 A | 5/1973 | Blackshear et al. | |
| 4,381,006 A | 4/1983 | Genese | |
| 4,525,165 A | 6/1985 | Fischell | |
| 4,557,728 A | 12/1985 | Sealfon et al. | |
| 4,608,042 A | 8/1986 | Vanderveen et al. | |
| 4,681,566 A | 7/1987 | Fenton, Jr. et al. | |
| 4,755,172 A | 7/1988 | Baldwin | |
| 4,772,263 A | 9/1988 | Dorman et al. | |
| 4,850,807 A | 7/1989 | Frantz | |
| 4,863,429 A | 9/1989 | Baldwin | |
| 5,007,556 A | 4/1991 | Lover | |
| 5,014,750 A | 5/1991 | Winchell et al. | |
| 5,098,377 A | 3/1992 | Borsanyi et al. | |
| 5,100,389 A | 3/1992 | Vaillancourt | |
| 5,176,641 A | 1/1993 | Idriss | |
| 5,201,717 A * | 4/1993 | Wyatt et al. | 604/192 |
| 5,205,820 A | 4/1993 | Kriesel | |
| 5,226,551 A | 7/1993 | Robbins, III | |
| 5,236,418 A | 8/1993 | Kriesel | |
| 5,290,259 A | 3/1994 | Fischer | |
| 5,306,257 A | 4/1994 | Zdeb | |
| 5,314,405 A | 5/1994 | Kriesel et al. | |
| 5,333,761 A | 8/1994 | Davis et al. | |
| 5,336,188 A | 8/1994 | Kriesel | |
| 5,346,476 A | 9/1994 | Elson | |
| 5,380,287 A | 1/1995 | Kikuchi et al. | |
| 5,411,480 A | 5/1995 | Kriesel | |

(Continued)

*Primary Examiner* — Nicholas D Lucchesi
*Assistant Examiner* — Jenna Zhang
(74) *Attorney, Agent, or Firm* — James E. Brunton

(57) ABSTRACT

A compact fluid dispenser for use in controllably dispensing fluid medicaments, such as analgesics and like medicinal agents from the device reservoir which is provided in the form of a novel bellows-type assembly. The fluid dispenser includes a unique stored energy mechanism that provides the force necessary to continuously and substantially uniformly expel fluid from the device reservoir. The device also includes a novel adjustable flow rate control assembly that is disposed intermediate the fluid reservoir outlet and the outlet port of the device for precisely controlling the rate of fluid flow from the outlet port toward the patient.

11 Claims, 29 Drawing Sheets

U.S. PATENT DOCUMENTS

| | | |
|---|---|---|
| 5,419,771 A | 5/1995 | Kriesel |
| 5,484,410 A | 1/1996 | Kriesel |
| 5,499,968 A | 3/1996 | Milijasevic et al. |
| 5,514,090 A | 5/1996 | Kriesel et al. |
| 5,545,139 A | 8/1996 | Kriesel |
| 5,620,420 A | 4/1997 | Kriesel |
| 5,632,406 A | 5/1997 | Robbins, III |
| 5,693,018 A | 12/1997 | Kriesel et al. |
| 5,693,019 A | 12/1997 | Kriesel |
| 5,720,729 A | 2/1998 | Kriesel |
| 5,721,382 A | 2/1998 | Kriesel et al. |
| 5,735,818 A | 4/1998 | Kriesel et al. |
| 5,741,242 A | 4/1998 | Kriesel |
| 5,743,879 A | 4/1998 | Kriesel |
| 5,766,149 A | 6/1998 | Kriesel et al. |
| 5,779,676 A | 7/1998 | Kriesel et al. |
| 5,807,323 A | 9/1998 | Kriesel et al. |
| 5,836,484 A | 11/1998 | Gerber |
| 5,858,005 A | 1/1999 | Kriesel |
| 5,885,250 A | 3/1999 | Kriesel et al. |
| 5,897,530 A | 4/1999 | Jackson |
| 5,921,962 A | 7/1999 | Kriesel et al. |
| 5,925,017 A | 7/1999 | Kriesel et al. |
| 5,957,891 A | 9/1999 | Kriesel et al. |
| 5,993,425 A | 11/1999 | Kriesel |
| 6,010,482 A | 1/2000 | Kriesel et al. |
| 6,027,472 A | 2/2000 | Kriesel et al. |
| 6,030,363 A | 2/2000 | Kriesel |
| 6,045,533 A | 4/2000 | Kriesel et al. |
| 6,063,059 A | 5/2000 | Kriesel |
| 6,068,613 A | 5/2000 | Kriesel et al. |
| 6,068,614 A | 5/2000 | Kimber et al. |
| 6,086,561 A | 7/2000 | Kriesel et al. |
| 6,090,071 A | 7/2000 | Kriesel |
| 6,095,491 A | 8/2000 | Kriesel |
| 6,126,637 A | 10/2000 | Kriesel et al. |
| 6,126,642 A | 10/2000 | Kriesel et al. |
| 6,152,898 A | 11/2000 | Olsen |
| 6,159,180 A | 12/2000 | Kriesel et al. |
| 6,176,845 B1 | 1/2001 | Kriesel et al. |
| 6,183,441 B1 | 2/2001 | Kriesel et al. |
| 6,190,359 B1 | 2/2001 | Heruth |
| 6,210,368 B1 | 4/2001 | Rogers |
| 6,236,624 B1 | 5/2001 | Kriesel et al. |
| 6,245,041 B1 | 6/2001 | Kriesel |
| 6,258,062 B1 | 7/2001 | Thielen et al. |
| 6,270,481 B1 | 8/2001 | Mason et al. |
| 6,273,133 B1 | 8/2001 | Williamson et al. |
| 6,277,095 B1 | 8/2001 | Kriesel et al. |
| 6,293,159 B1 | 9/2001 | Kriesel et al. |
| 6,319,235 B1 | 11/2001 | Yoshino |
| 6,332,876 B1 * | 12/2001 | Poynter et al. ................ 604/212 |
| 6,355,019 B1 | 3/2002 | Kriesel et al. |
| 6,391,006 B1 | 5/2002 | Kriesel et al. |
| 6,394,980 B2 | 5/2002 | Kriesel et al. |
| 6,398,760 B1 | 6/2002 | Danby |
| 6,416,495 B1 * | 7/2002 | Kriesel et al. ................ 604/132 |
| 6,485,461 B1 | 11/2002 | Mason et al. |
| 6,537,249 B2 | 3/2003 | Kriesel et al. |
| 6,542,350 B1 | 4/2003 | Rogers |
| 6,569,125 B2 | 5/2003 | Jepson et al. |
| 6,645,175 B2 | 11/2003 | Kriesel et al. |
| 6,669,668 B1 | 12/2003 | Kleeman et al. |
| 7,029,455 B2 | 4/2006 | Flaherty |
| 2005/0277882 A1 * | 12/2005 | Kriesel ........................ 604/131 |
| 2007/0219501 A1 * | 9/2007 | Kriesel et al. ................ 604/185 |

\* cited by examiner

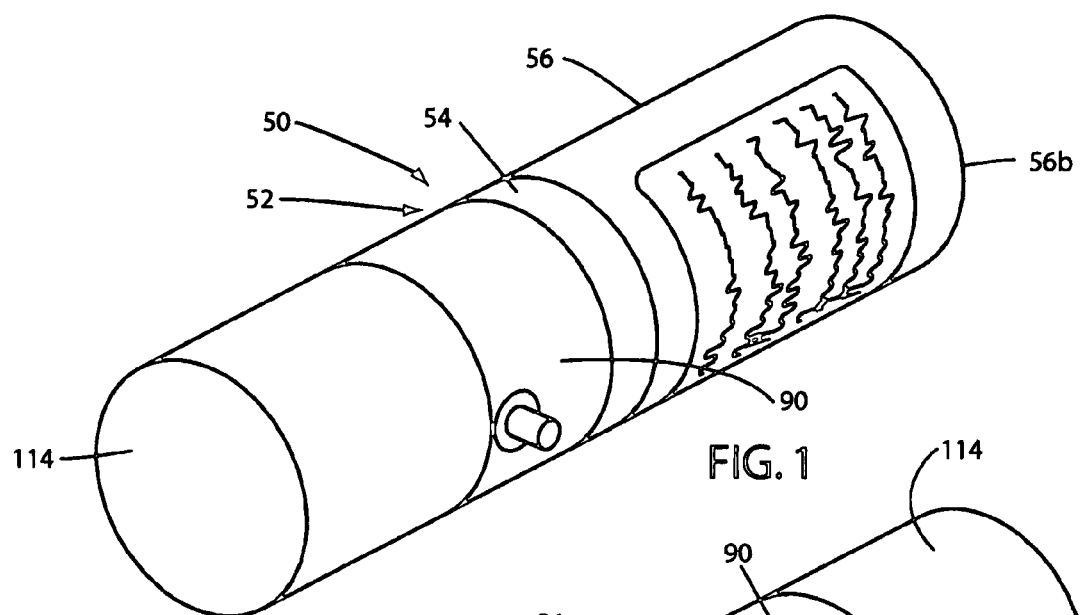
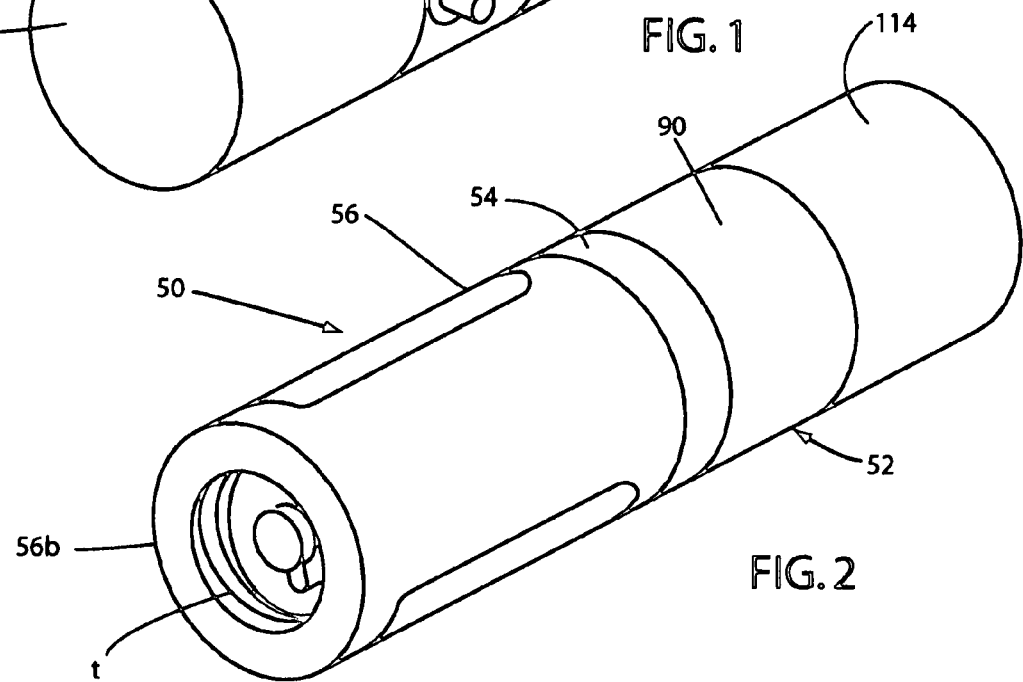

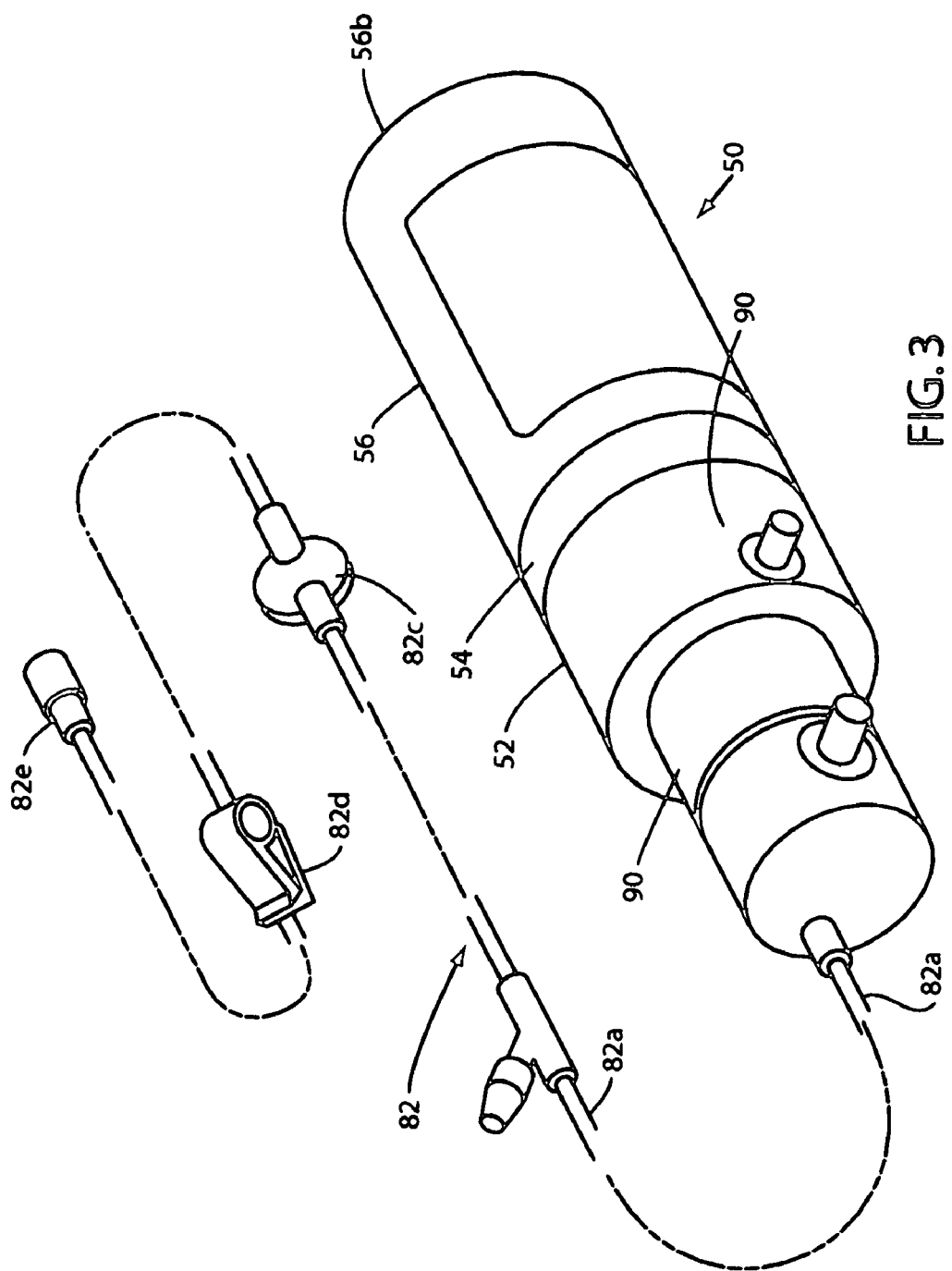

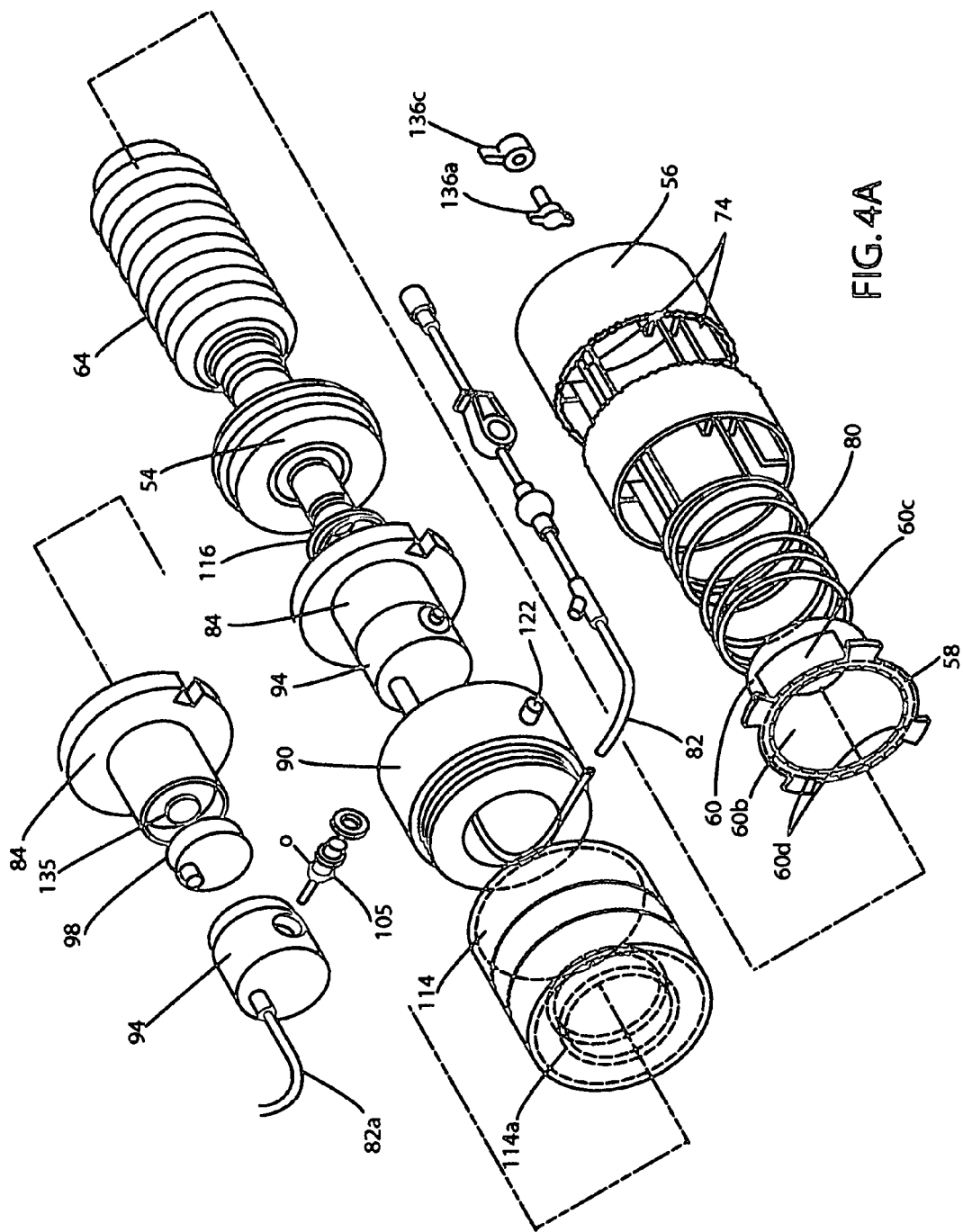

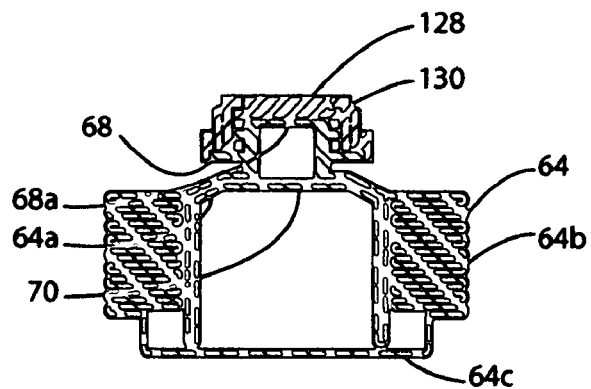
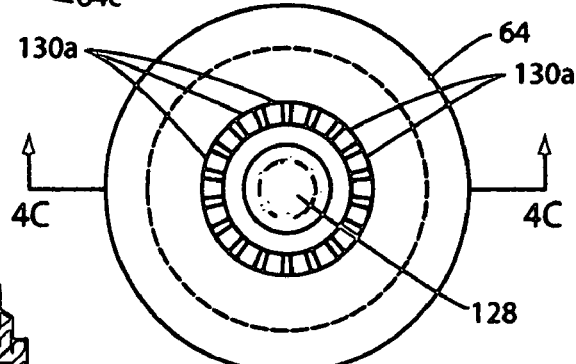
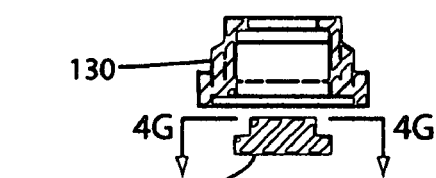
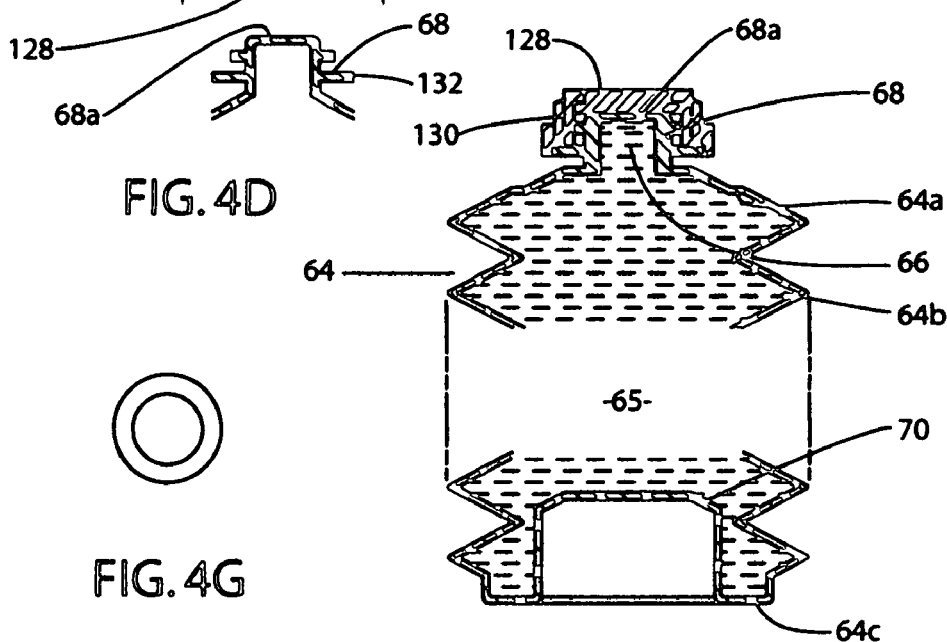
FIG. 4E
FIG. 4B
FIG. 4D
FIG. 4G
FIG. 4C

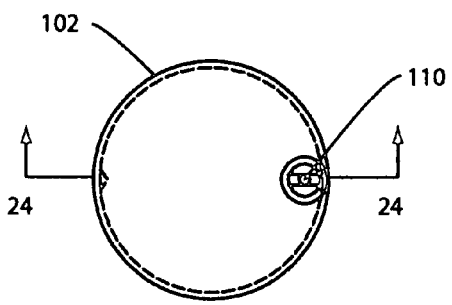
FIG. 23
FIG. 24
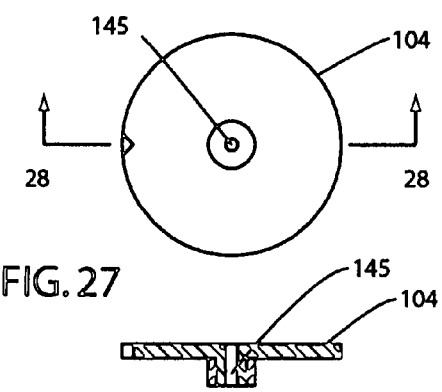
FIG. 27
FIG. 28
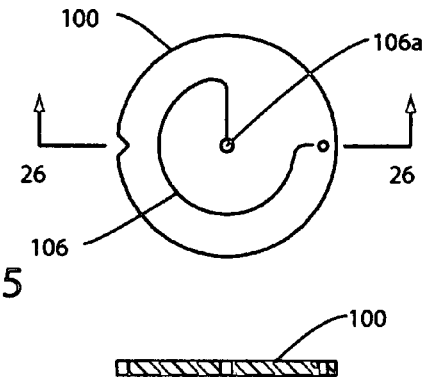
FIG. 25
FIG. 26

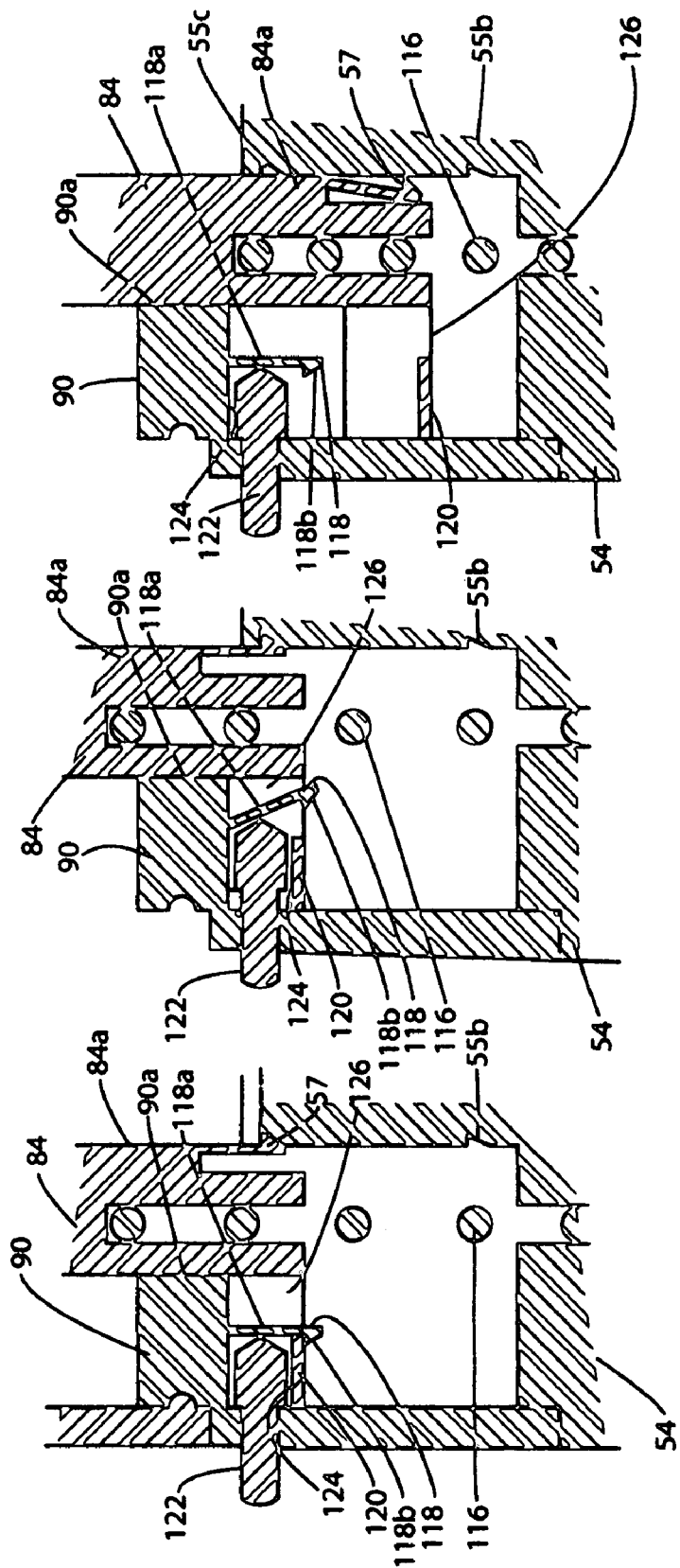

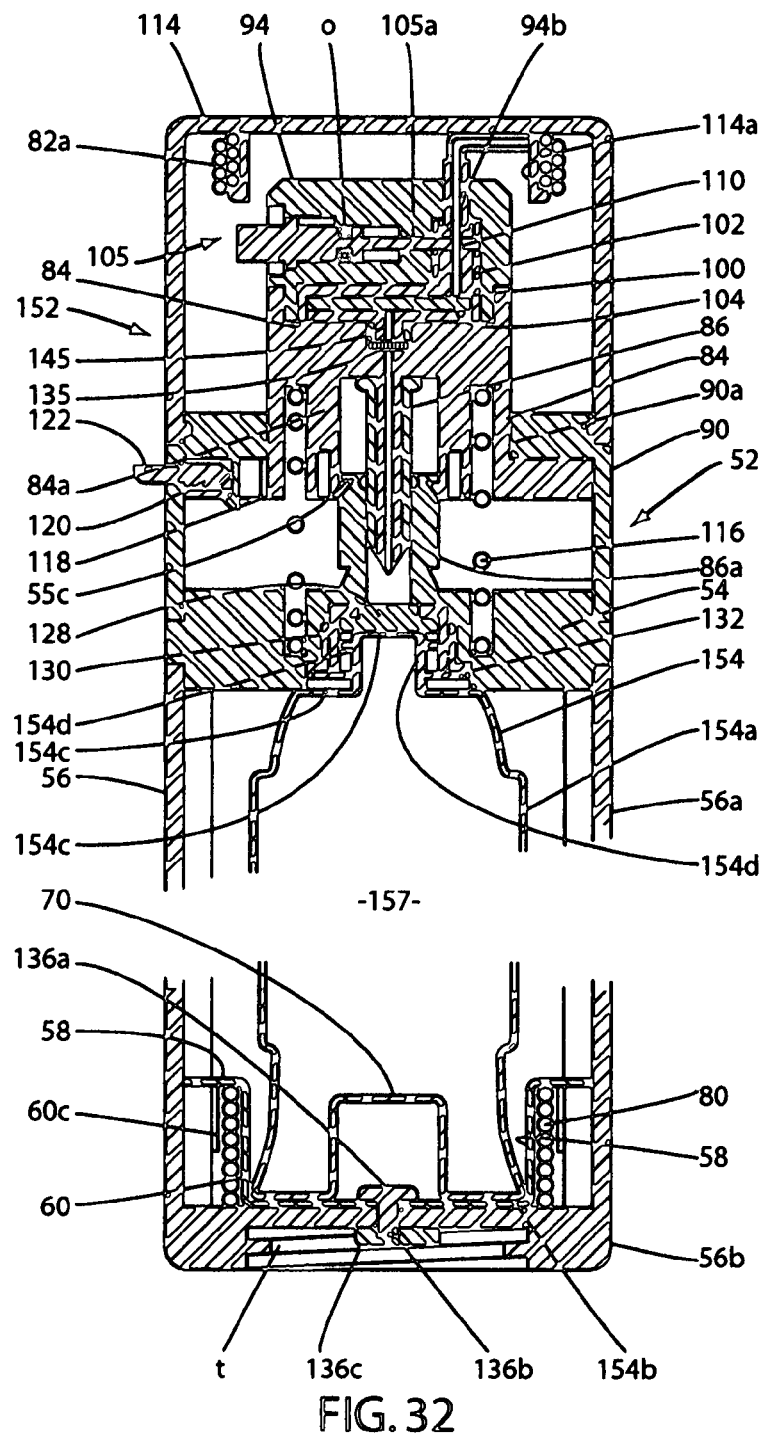
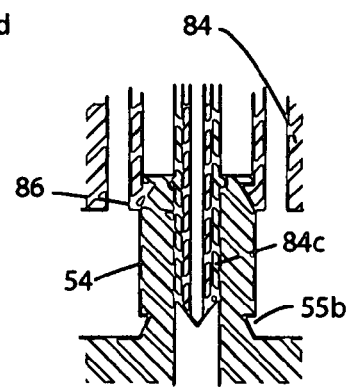
FIG. 32
FIG. 32A

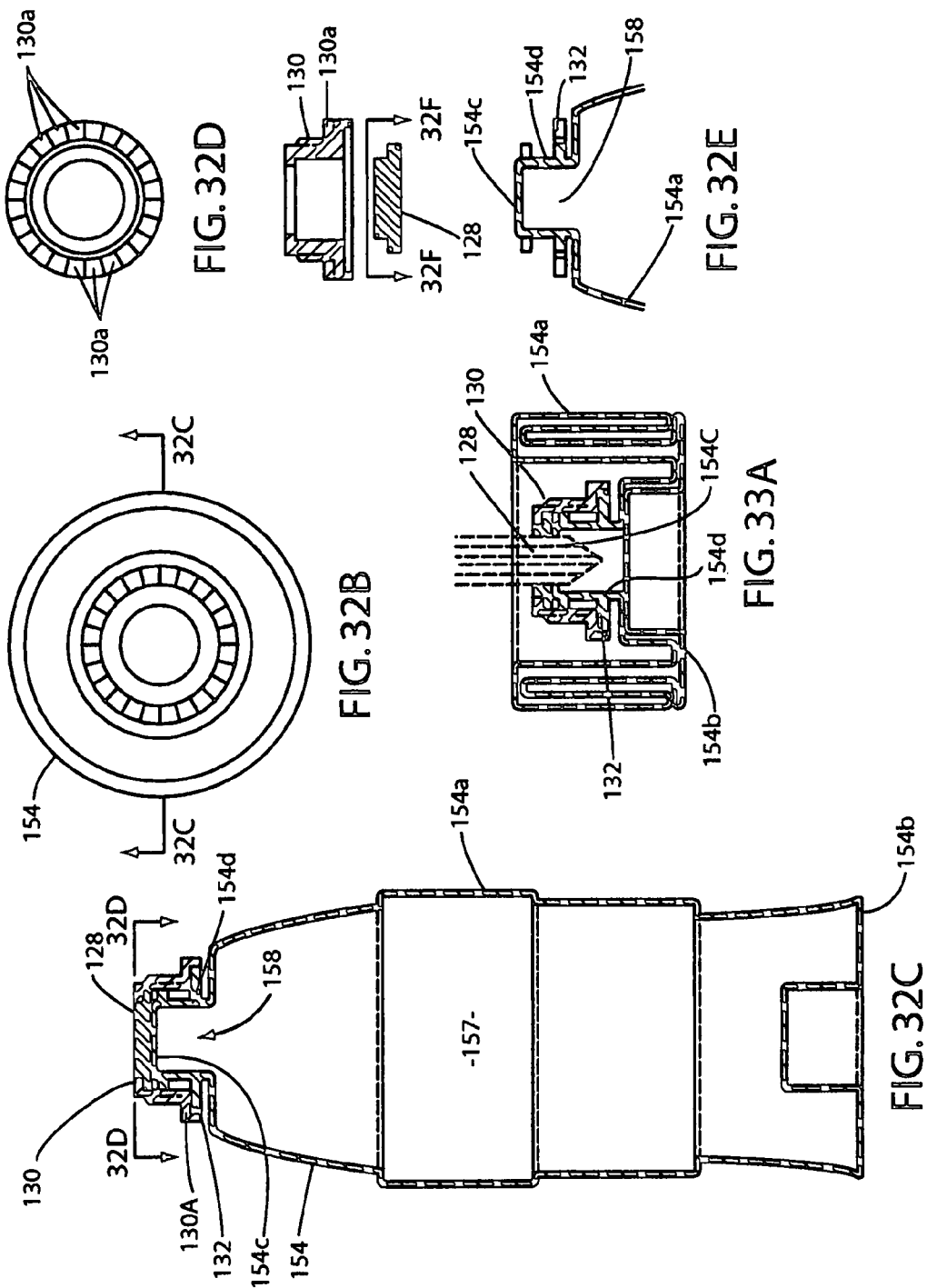

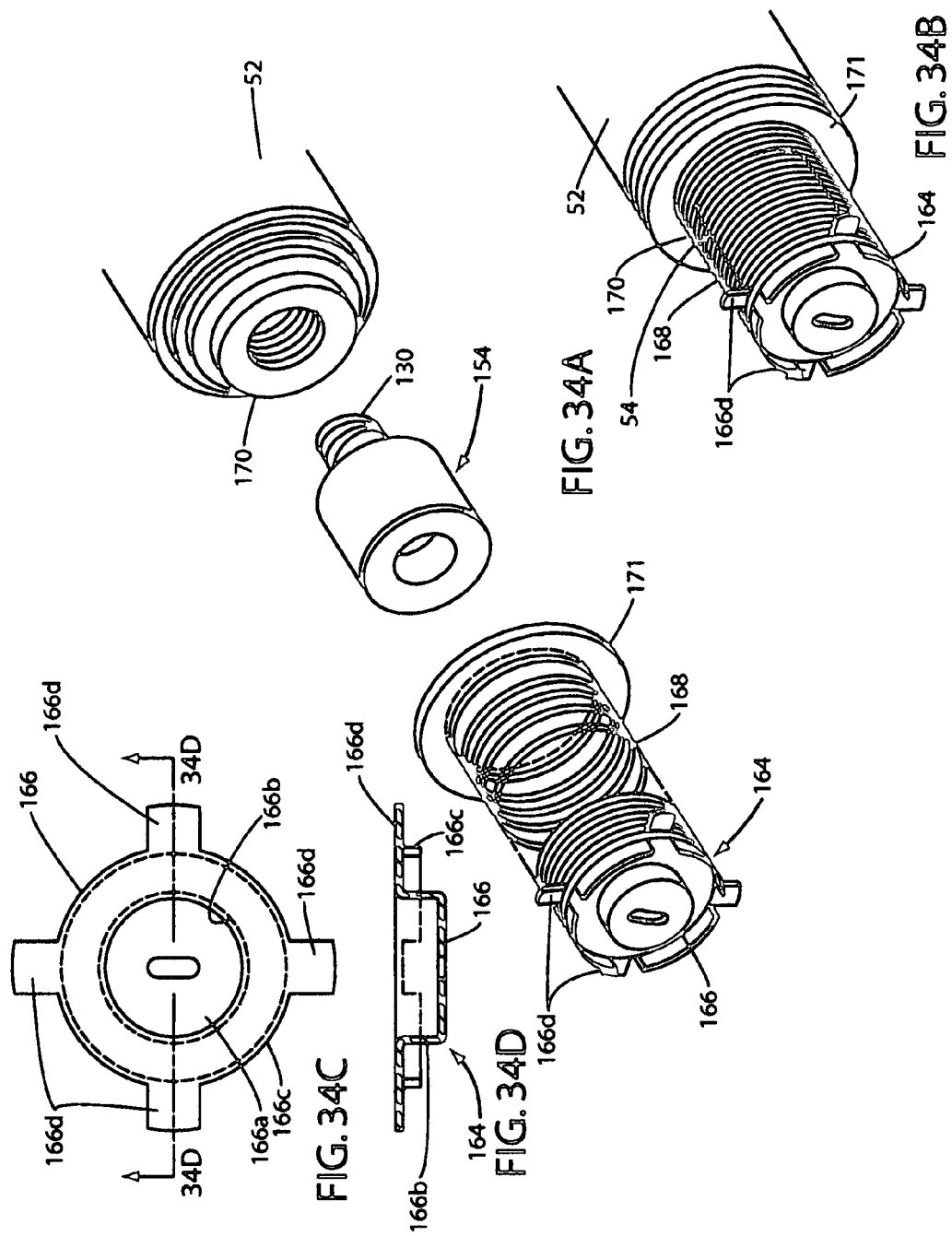

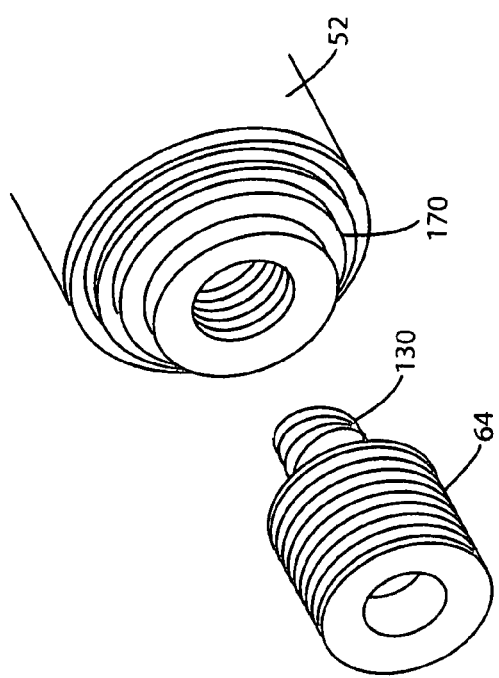
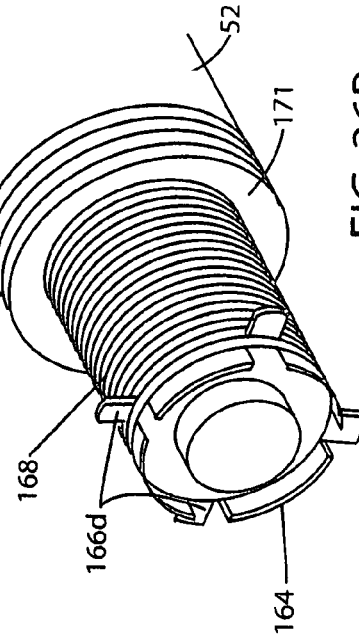
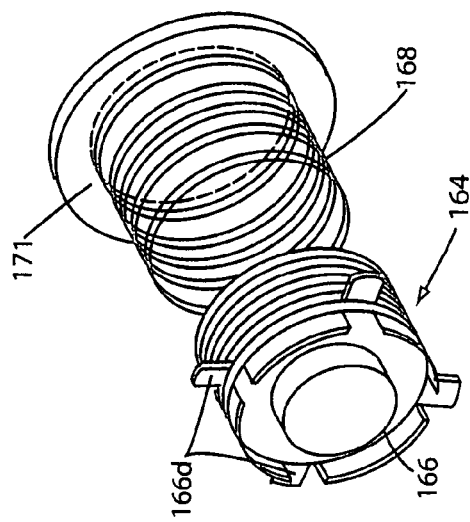
FIG. 36A
FIG. 36B

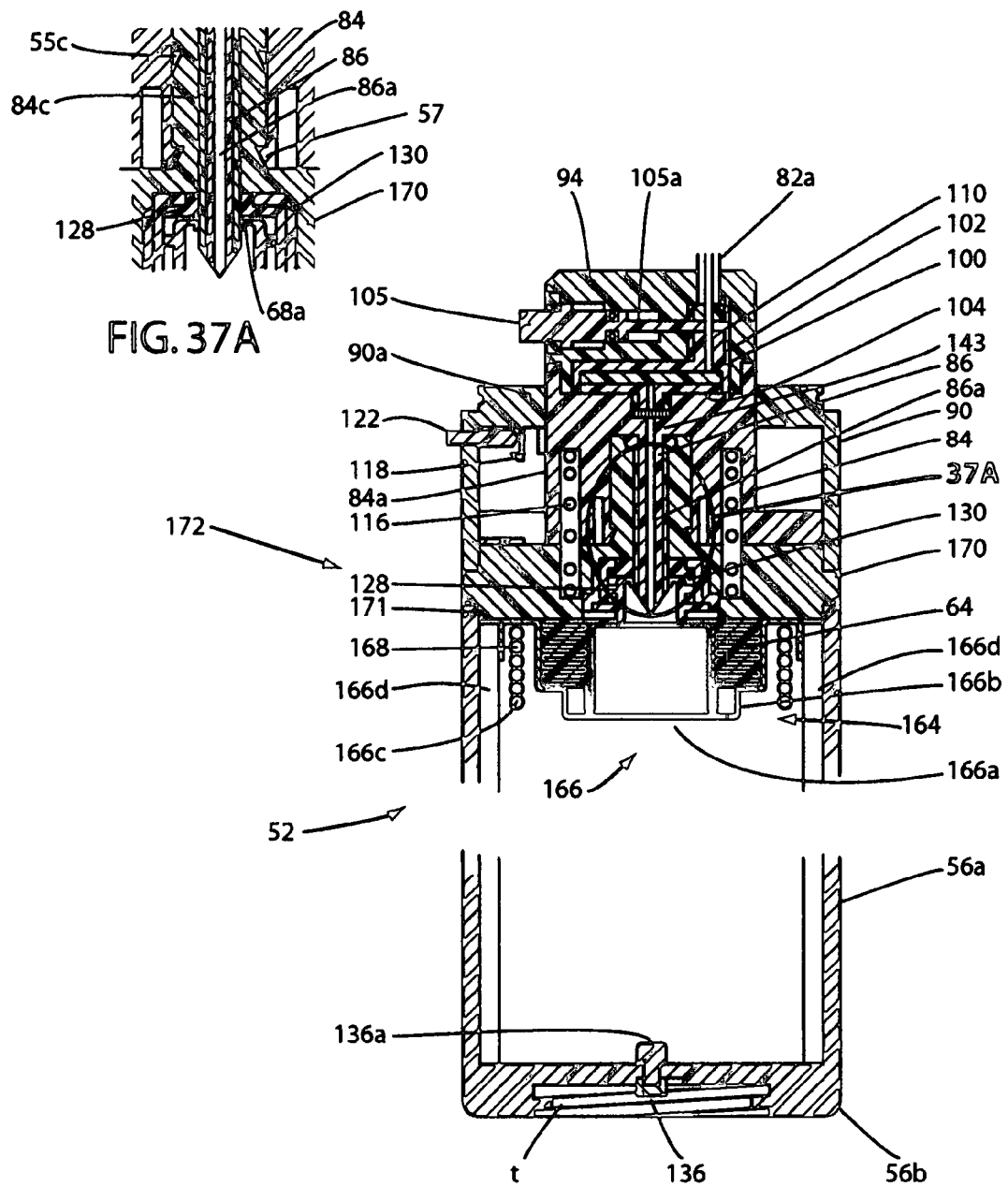

FLUID DISPENSER

This is a Non-Provisional Application claiming the benefit of Provisional Application No. 60/834,770 filed Jul. 31, 2006.

BACKGROUND OF THE INVENTION

1. Field of the Invention

The present invention relates generally to fluid dispensing devices. More particularly, the invention concerns an improved apparatus for infusing medicinal agents into an ambulatory patient at specific rates over extended periods of time which includes a novel actuating mechanism and a unique adjustable flow rate control means for precisely, adjustably controlling the rate of fluid flow from the reservoir of the device toward the patient.

2. Discussion of the Prior Art

Many medicinal agents require an intravenous route for administration of the medicament. The delivery device for delivering the medicament, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reactions.

In the past, prolonged infusion of fluids has generally been accomplished using gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus. Devices from which liquid is expelled from a relatively thick-walled bladder by internal stresses within the distended bladder are well known in the prior art. Such bladder, or "balloon"-type, devices are described in U.S. Pat. No. 3,469,578 issued to Bierman and in U.S. Pat. No. 4,318,400 issued to Perry.

One of the most versatile and unique fluid delivery apparatus developed in recent years is that developed by one of the present inventors and described in U.S. Pat. No. 5,205,820. The components of this novel fluid delivery apparatus generally includes: a base assembly, an elastomeric membrane serving as a stored energy means, fluid flow channels for filling and delivery, flow control means, a cover, and an ullage which comprises a part of the base assembly.

Another prior art patent issued to one of the present applicants, namely U.S. Pat. No. 5,743,879, discloses an injectable medicament dispenser for use in controllably dispensing fluid medicaments such as insulin, anti-infectives, analgesics, oncolylotics, cardiac drugs biopharmaceuticals, and the like from a pre-filled container at a uniform rate. The dispenser, which is quite dissimilar in construction and operation from that of the present invention, includes a stored energy source in the form of a compressively deformable, polymeric, elastomeric member that provides the force necessary to controllably discharge the medicament from a pre-filled container which is housed within the body of the device. After having been deformed, the polymeric, elastomeric member will return to its starting configuration in a highly predictable manner.

Another important prior art fluid delivery device is described in U.S. Pat. No. 6,063,059 also issued to one the present inventors. This device, while being of a completely different construction, embodies a compressible-expandable stored energy source somewhat similar to that used in the apparatus of the present invention.

As will be appreciated from the discussion which follows, the apparatus of the present invention is uniquely suited to provide precise, continuous fluid delivery management at a low cost in those cases where a variety of precise dosage schemes are of utmost importance. An important aspect of the apparatus of the present invention is the provision of a novel rotatable fluid flow rate control means that includes uniquely formed micro-capillary, multi-channel flow rate control channels which enable precise control of the rate of fluid flow of the medicament to the patient. More particularly, the apparatus of the present invention includes a novel adjustable fluid flow rate mechanism which enables the fluid contained within the reservoir of the device to be precisely dispensed at various selected rates.

The apparatus of the present invention can be used with minimal professional assistance in an alternate health care environment such as the home. By way of example, devices of the invention can be comfortably and conveniently removably affixed to the patient's body or clothing and can be used for the continuous infusion of analgesics and can be manufactured in both low flow and high flow configurations.

By way of summary, the apparatus of the present invention uniquely overcomes the drawbacks of the prior art by providing a novel, disposable dispenser of simple but highly reliable construction. A particularly important aspect of the apparatus of the present invention resides in the provision of a novel, self-contained energy source in the form of a compressible-expandable spring member that provides the force necessary to substantially, uniformly dispense various solutions from the device reservoir. Because of the simplicity of construction of the apparatus of the invention, and the straightforward nature of the energy source, the apparatus can be manufactured at low cost without in any way sacrificing accuracy and reliability.

SUMMARY OF THE INVENTION

It is an object of the present invention to provide a compact fluid dispensing device for use in controllably dispensing fluid medicaments, such as, diluents, analgesics, and like medicinal agents from the novel, prefilled bellows-type device reservoir.

It is another object of the invention to provide a fluid dispenser of the aforementioned character which is highly reliable and is easy-to-use by laypersons in a non-hospital environment.

Another object of the invention is to provide a small, compact fluid dispenser that includes a novel actuating mechanism controllably delivering to the patient the medicament contained within the device reservoir.

Another object of the invention is to provide an apparatus which can be factory pre-filled with a wide variety of medicinal fluids that can be easily dispensed in the field.

Another object of the invention is to provide a dispenser in which a stored energy source is provided in the form of a spring member of novel design that provides the force necessary to continuously and substantially uniformly expel fluid from the device reservoir.

Another object of the invention is to provide a device of the aforementioned character which includes novel adjustable flow rate control means disposed intermediate the fluid reservoir outlet and the outlet port of the device for precisely controlling the rate of fluid flow from the outlet port toward the patient.

Another object of the invention is to provide a fluid dispenser of the class described which is compact, lightweight, is easy for ambulatory patients to use, is fully disposable, and is extremely accurate so as to enable the infusion of precise doses of medicament over prescribed periods of time.

Another object of the invention is to provide a device of the character described which embodies a novel, easy to use disabling mechanism.

Another object of the invention is to provide a self-contained medicament dispenser which is of very simple construction and yet extremely reliable in use.

Another object of the invention is to provide a fluid dispenser as described in the preceding paragraphs which is easy and inexpensive to manufacture in large quantities.

BRIEF DESCRIPTION OF THE DRAWINGS

FIG. 1 is a generally perspective, top view of one form of the fluid dispenser of the present invention showing one side of the device.

FIG. 2 is a generally perspective, bottom view of the fluid dispensing device shown in FIG. 1 showing the opposite side of the device.

FIG. 3 is a generally perspective, top view of the fluid-dispensing device shown in FIGS. 1 and 2, but with the closure cap removed to permit access to the administration set.

FIG. 4A is a generally perspective, exploded view of the fluid-dispensing device shown in FIG. 4.

FIG. 4B is a top plan view of one form of the bellows-type reservoir defining assembly of the invention.

FIG. 4C is a foreshortened, cross-sectional view taken along lines 4C-4C of FIG. 4B.

FIG. 4D is a fragmentary, cross-sectional, exploded view of the neck portion of the reservoir defining assembly illustrated in FIG. 4C.

FIG. 4E is a cross-sectional view similar to FIG. 4C, but showing the reservoir defining assembly in a collapsed configuration.

FIG. 4G is a view taken along lines 4G-4G of FIG. 4D.

FIG. 23 is a top plan view of the rate control cover of the rate control disabling assembly.

FIG. 24 is a cross-sectional view taken along lines 24-24 of FIG. 23.

FIG. 25 is a top plan view of the rate control plate of the rate control assembly.

FIG. 26 is a cross-sectional view taken along lines 26-26 of FIG. 25.

FIG. 27 is a top plan view of the bottom closure plate of the rate control disabling assembly.

FIG. 28 is a cross-sectional view taken along lines 28-28 of FIG. 27.

FIG. 29 is a greatly enlarged, fragmentary, cross-sectional view of a portion of the flow control means of one form of the invention.

FIG. 30 is a view similar to FIG. 29, but showing the actuation of the release mechanism to permit downward movement of the penetrating member housing.

FIG. 31 is a view similar to FIG. 30, but showing the appearance of the components of the device following the release of the release mechanism and the downward movement of the penetrating member housing.

FIG. 32 is a longitudinal, cross-sectional view of an alternate form of the dispensing device of the invention illustrating a different type of collapsible reservoir defining component.

FIG. 32A is an enlarged, fragmentary, cross-sectional view of a portion of the penetrating member housing and of the connector member of the apparatus of this latest form of the invention.

FIG. 32B is a top plan view of one form of the collapsible-bottle-type reservoir defining assembly of this latest form of the invention.

FIG. 32C is a cross-sectional view taken along lines 32C-32C of FIG. 32B.

FIG. 32D is a view taken along lines 32D-32D of FIG. 32C.

FIG. 32E is a fragmentary, cross-sectional, exploded view of the neck portion of the reservoir defining assembly illustrated in FIG. 32C.

FIG. 33A is a cross-sectional view similar to FIG. 32C, but showing the reservoir defining assembly of this latest form of the invention in a collapsed configuration.

FIG. 34A is a generally perspective, exploded view of the carriage assembly, the stored energy means, the foreshortened reservoir defining means and a portion of the outer housing of the form of the invention shown in FIG. 34.

FIG. 34B is a generally perspective view similar to FIG. 34A, but showing the components illustrated in FIG. 34A as they appear when interconnected.

FIG. 34C is a top plan view of the carriage of this latest form of the invention.

FIG. 34D is a cross-sectional view taken along lines 34D-34D of FIG. 34C.

FIG. 36A is a generally perspective, exploded view of the carriage assembly, the stored energy means, the reservoir defining means and a portion of the outer housing of the form of the invention shown in FIG. 34.

FIG. 36B is a generally perspective view similar to FIG. 36A, but showing the components illustrated in FIG. 36A as they appear when interconnected.

FIG. 37 is a longitudinal, cross-sectional view similar to FIG. 36, but showing the appearance of the device following the fluid dispensing step.

FIG. 37A is a fragmentary, cross-sectional view of the area designated in FIG. 37 as 37A.

DISCUSSION OF THE INVENTION

Figure 4:
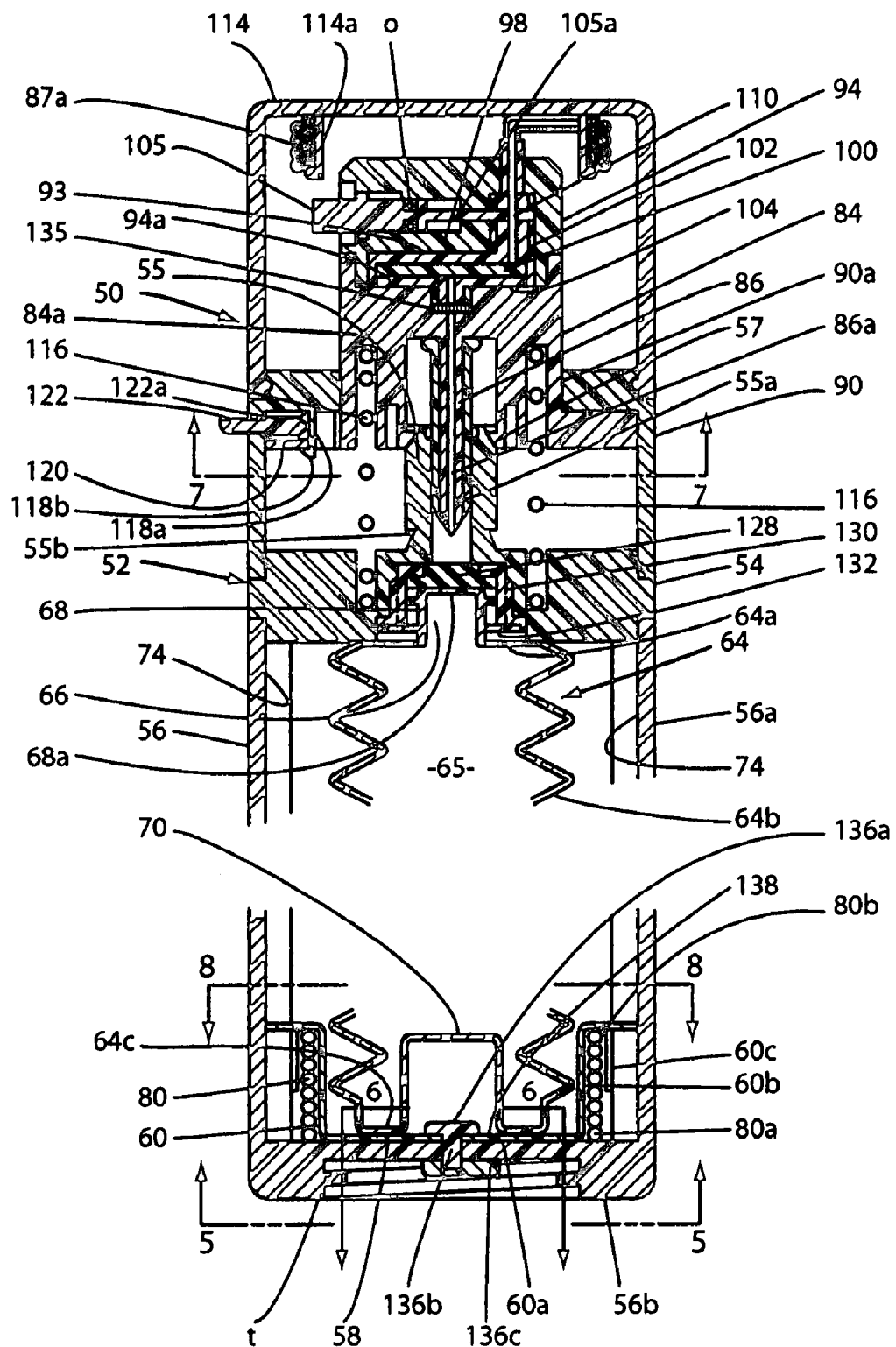
FIG. 4 is a longitudinal, cross-sectional view of the fluid-dispensing device shown in FIGS. 1 and 2.

Referring to the drawings and particularly to FIGS. 1 through 4A, one form of the dispensing device of the present invention for dispensing medicaments to a patient is there shown and generally designated by the numeral 50. The dispensing device here includes a supporting structure 52, which includes a connector assembly 54 (See FIGS. 4 and 4A) and a generally cylindrically shaped main housing 56 that is interconnected with the connector assembly in the manner best seen in FIG. 4 of the drawings. Supporting structure 52 can be constructed from metal, plastic or any suitable material. Main housing 56 includes a generally cylindrically shaped wall portion 56a and a threaded base portion 56b having threads "T" for attachment thereto of auxiliary hanger devices.

Figure 9:
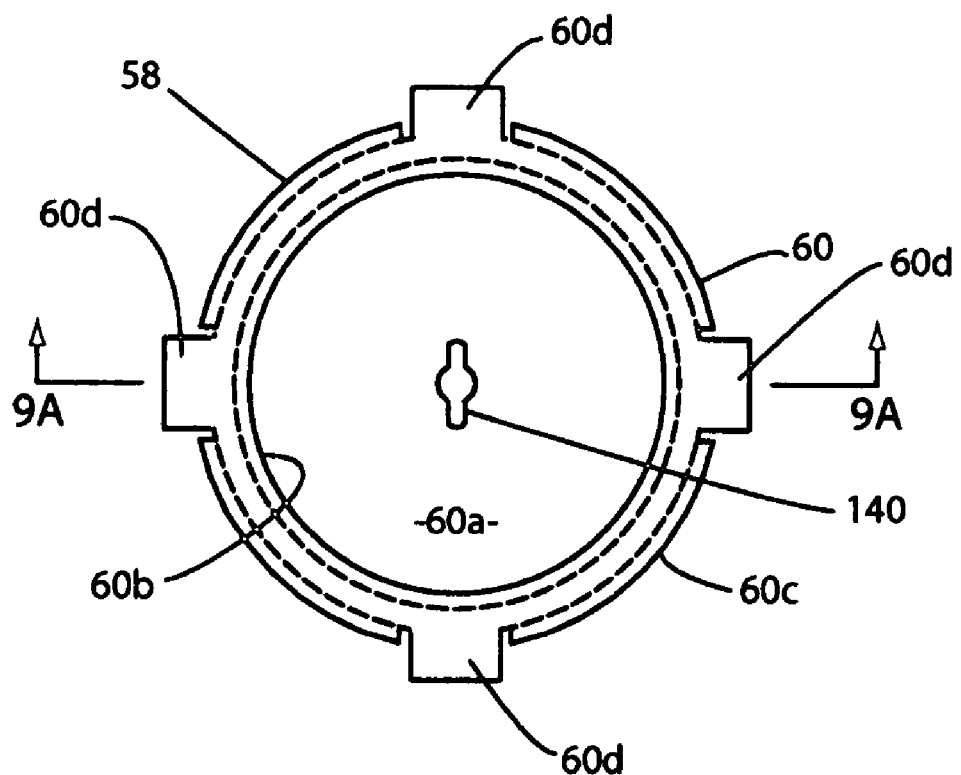
FIG. 9 is a top plan view of the carriage component of the device.
Figure 9A:
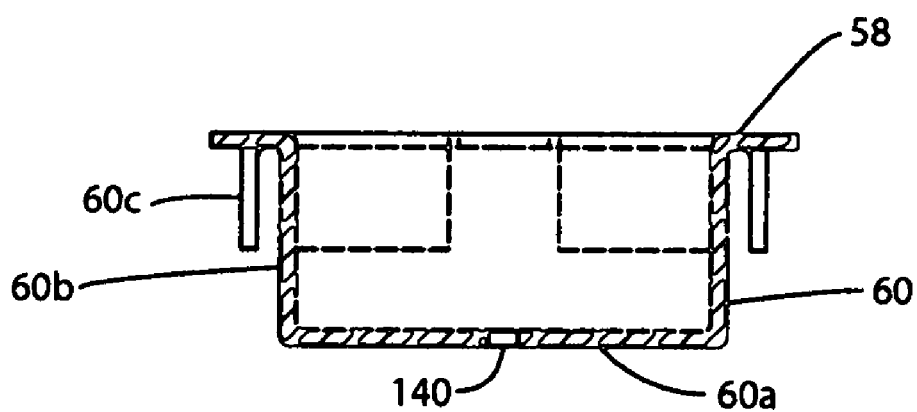
FIG. 9A is a cross-sectional view taken along lines 9A-9A of FIG. 9.
Figure 10:
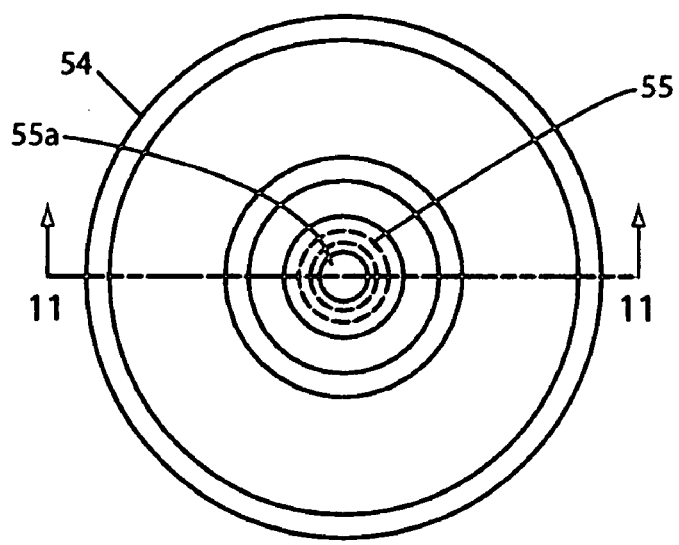
FIG. 10 is a top plan view of the dispenser housing cover component of the device.

Disposed within wall portion 56a is a carriage assembly 58, which is movable between a first position, shown in FIG. 4, and a second position, shown in FIG. 4A. As best seen by referring to FIGS. 4, 9 and 9A, carriage assembly 58 comprises a carriage 60 having a carriage base 60a and a generally cylindrically shaped sidewall 60b which terminates in a radially outwardly and downwardly extending flange 60c. As best seen in FIG. 9A, flange 60c includes a plurality of circumferentially spaced guide tabs 60d, the purpose of which will presently be described. Carriage assembly 58 is releasably locked in its first position by a novel locking means the character of which will be described in the paragraphs that follow.

Carried by carriage assembly 58 is a reservoir defining, semi-rigid assembly 64 that defines a fluid reservoir 65. As indicated in FIGS. 4, 4C and 4D reservoir 65 has a combination inlet/outlet 66 that is formed in a neck portion 68. Neck portion 68, which includes a closure wall 68a, is connected to a top wall 64a of the reservoir defining assembly 64, which, in turn, is connected to an accordion-like side wall 64b. Wall 64b is connected to a bottom wall 64c that includes an upstanding ullage portion 70. Top wall 64a, closure wall 68a, side wall 64b and bottom wall 64c cooperate to define the fluid reservoir 65. It is to be understood that top wall 64a, side wall 64b and bottom wall 64c can be circular, oval or of various other desired shapes; similarly, main housing 54 can be of various shapes comparable with the reservoir defining assembly.

In the preferred form of the invention, reservoir defining assembly 64 is constructed in accordance with an aseptic blow-fill seal technique of a character well understood by those skilled in the art. This aseptic blow-fill seal technique typically involves the continuous plastic extrusion through an extruder head of a length of parison in the form of a hollow tube between and through two co-acting first or main mold halves. The technique includes the step of cutting off the parison below the extruder head and above the main mold halves to create an opening which allows a blowing and filling nozzle assembly to be moved downwardly into the opening in the parison for molding and thereafter filling a molded container.

When the container is filled with the desired amount of fluid, the blowing and filling nozzle assembly is retracted from the opening in the parison. A separate pair of co-acting second or upper sealing mold halves are then moved together around the exposed length of parison to form and seal the upper portion of the container. The finished container, completely formed, filled, and sealed to form a pre-filled container is then conveyed out of the apparatus. The pre-filled container may contain an injectable medicament or a parental fluid. Further information concerning aseptic blow-fill techniques is available from Weiler Engineering of Elgin, Ill. and Rommelag of Stutgart, Germany.

Figure 4F:
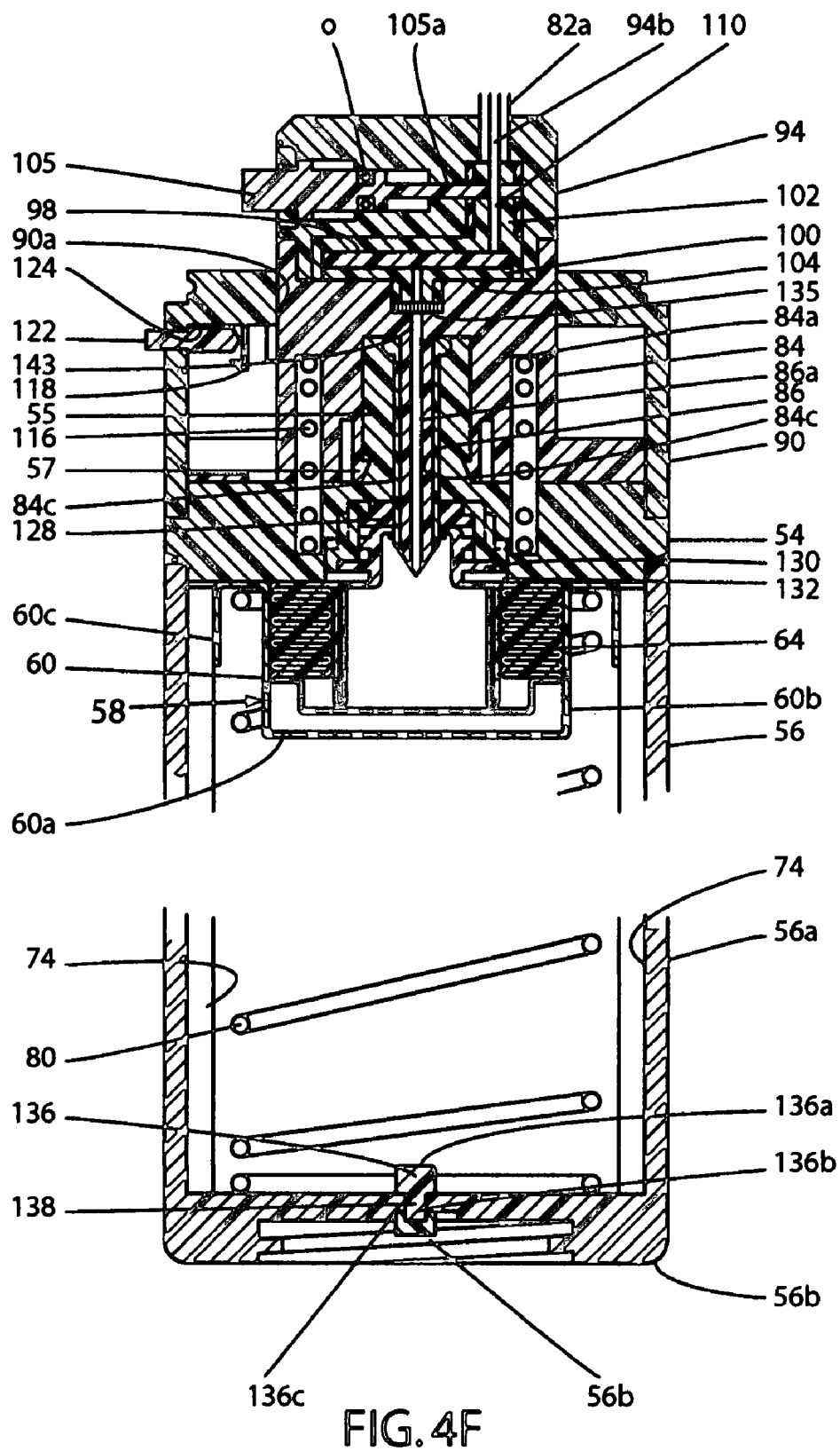
FIG. 4F is a longitudinal, cross-sectional view similar to FIG. 4, but showing the device as it appears following the fluid dispensing step.
Figure 5:
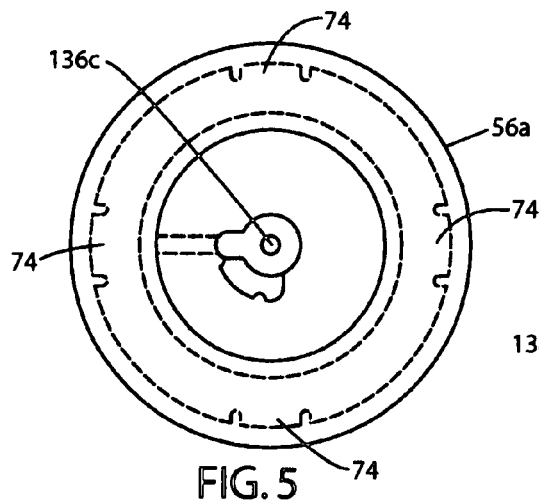
FIG. 5 is a view taken along lines 5-5 of FIG. 4.
Figure 6:
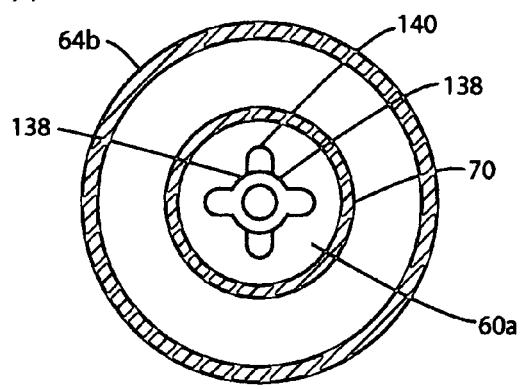
FIG. 6 is a cross-sectional view taken along lines 6-6 of FIG. 4.
Figure 7:
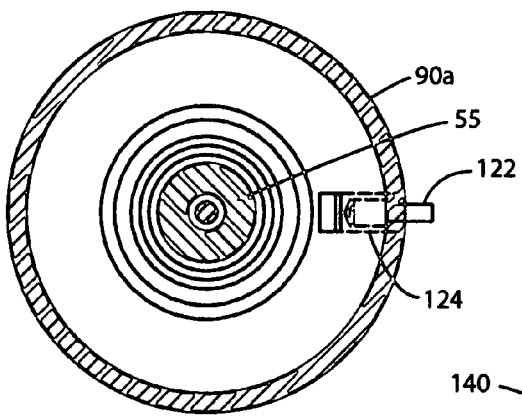
FIG. 7 is a cross-sectional view taken along lines 7-7 of FIG. 4.
Figure 8:
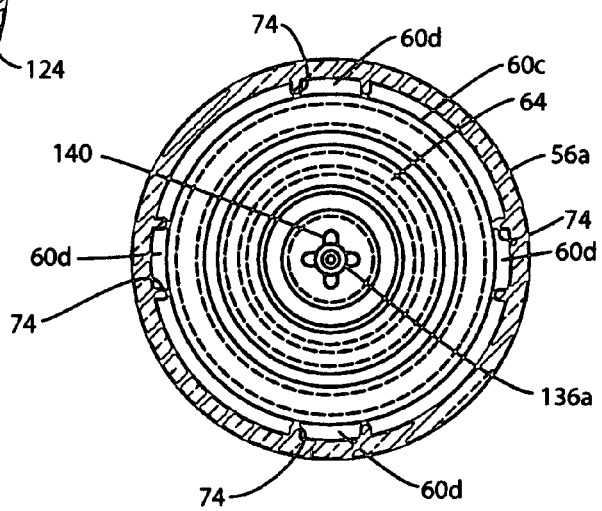
FIG. 8 is a cross-sectional view taken along lines 8-8 of FIG. 4.
Figure 16:
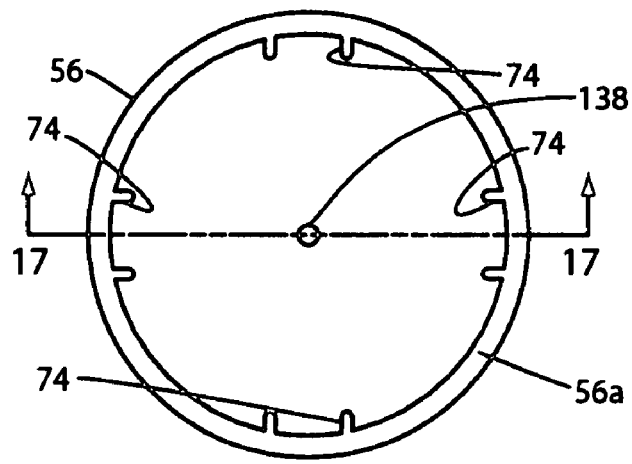
FIG. 16 is a top plan view of the main dispenser housing component of the device of the invention.

An important feature of the present invention resides in the provision of guide means for guiding travel of carriage assembly 58 between the first position shown in FIG. 4 and the second position shown in FIG. 4F. In the present form of the invention this important guide means comprises a plurality of circumferentially spaced guide channels 74 which are formed with and extend inwardly from generally cylindrically shaped wall portion 56a (FIGS. 5, 8 and 16). As indicated in FIG. 8, guide tabs 60d are slidably received within the interior wall portion guide channels 74 so that as the carriage assembly travels from its first position toward its second position, guide channels 74 precisely guide its travel.

To controllably move the carriage assembly from its first position to its second position, novel stored energy means are provided. This novel stored energy means, which is operably associated with carriage assembly 58, is here provided in the form of a coiled spring 80. As illustrated in FIGS. 4 and 4A, one end 80a of the coil spring 80 is disposed in engagement with the threaded base portion 56b of the main, or outer, housing 56 of the supporting structure and the other end 80b thereof is disposed in engagement with flange 60c of carriage 60. With this construction, after operation of the reservoir accessing means in a manner presently to be described and when the locking means of the invention is manipulated in a manner to unlock the carriage assembly from base portion 56b of the main housing, spring 80 will be allowed to move from its retracted position shown in FIG. 4 to its expanded position shown in FIG. 4F, and in so doing will controllably move the carriage assembly from its starting position shown in FIG. 4 to its fully deployed or extended position shown in FIG. 4F. As will be described more fully in the paragraphs which follow, after operation of the reservoir accessing means, as the carriage assembly moves toward its deployed position, the accordion sidewall 64b of the bellows member 64 will move into the collapsed configuration shown in FIGS. 4E and 4F and in so doing will cause the medicinal fluid contained within the container to be controllably expelled therefrom.

To further control the flow of medicinal fluid from reservoir 65 toward the administration set 82 of the invention (FIG. 3) and then on to the patient, flow control means are provided. This novel fluid flow control means, which is carried by connector assembly 54 of the supporting structure 52, is controllably movable from the first position shown in FIG. 4 to the second position shown in FIG. 4F. This important fluid flow control means here comprises two cooperating components, namely a rate control means for controlling the rate of fluid flow from the collapsible reservoir and a reservoir accessing means for accessing the collapsible reservoir of the device and for controlling fluid flow between the collapsible reservoir and the rate control means.

Figure 14:
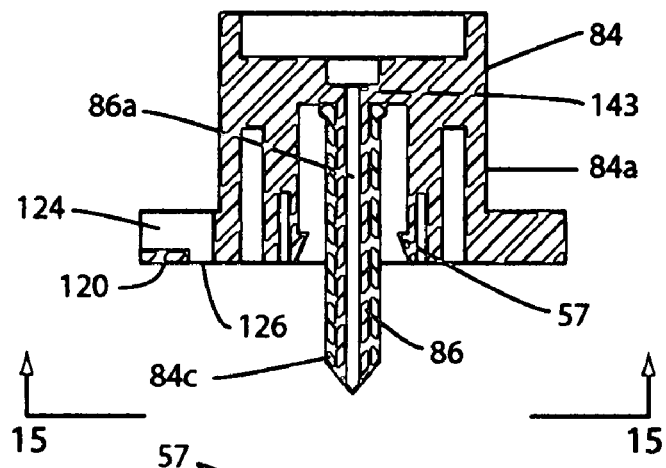
FIG. 14 is a cross-sectional view taken along lines 14-14 in FIG. 13.

The reservoir accessing means, which will be discussed in greater detail hereinafter, here comprises a penetrating member housing 84, which includes a penetrating member 86 (FIGS. 4 and 14). Penetrating member housing 84 is operably associated with an upper housing 90 (FIGS. 4 and 20), which is, in turn, carried by connecter member 54 in the manner shown in FIG. 4.

Figure 22:
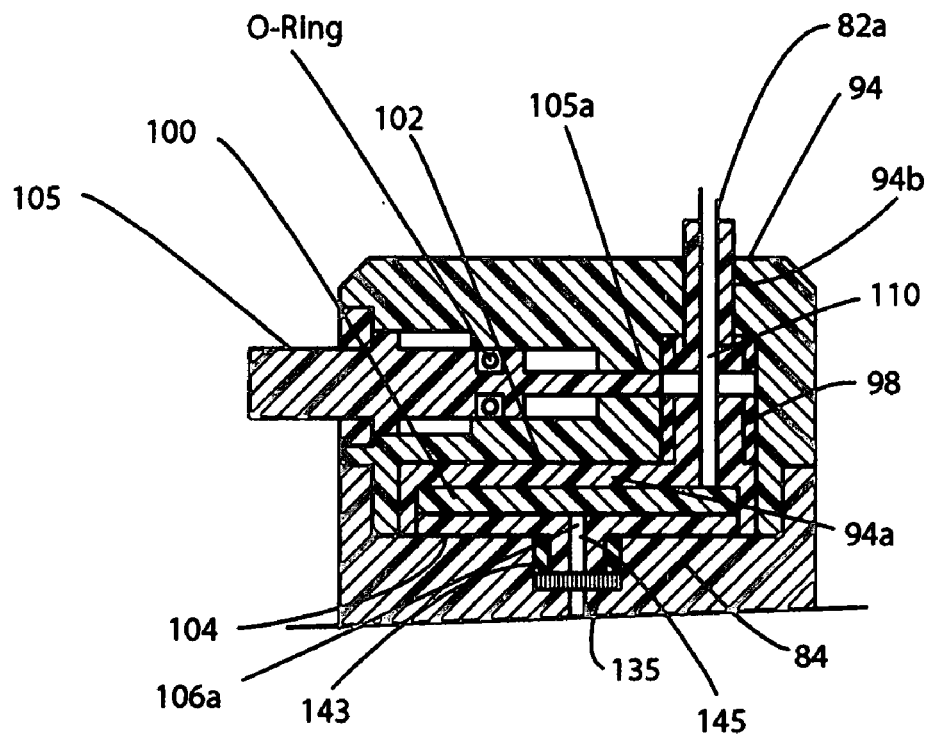
FIG. 22 is a cross-sectional view of the rate control and disabling assembly of the apparatus.

The rate control means of the invention, which is illustrated in FIGS. 22 through 28, includes a rate control housing 94 that is carried by penetrating member housing 84 in the manner illustrated in FIG. 4. As best seen in FIG. 22, rate control housing 94 is provided with a cavity 94a within which the novel rate control assembly 98 of the invention is disposed. Rate control assembly 98 here comprises a novel rate control plate 100 (FIGS. 25 and 26) that is held captive between the lower surface 93 of the first rate control cover and the second mating rate control cover 104 (FIGS. 24 and 28). As will presently be described, rate control plate 100 is provided with a circuitous fluid flow micro-channel 106 having an inlet 106a (FIG. 25) that is in fluid communication with outlet 66 of collapsible reservoir 65.

Figure 22A:
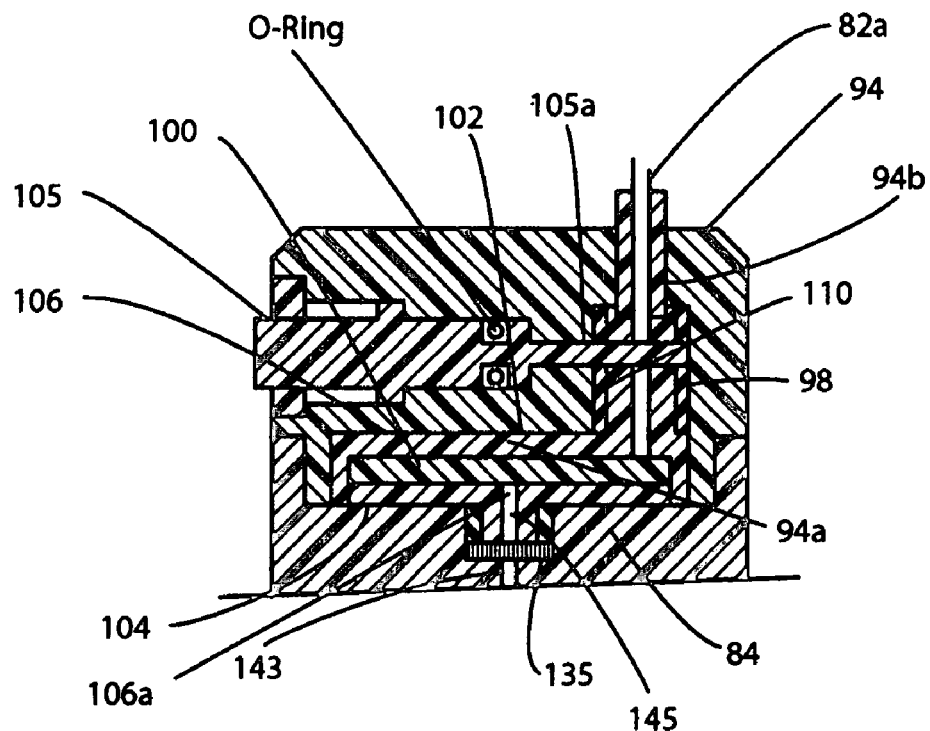
FIG. 22A is a cross-sectional view similar to FIG. 22, but showing the system disabled.

Also housed within rate control housing 94 is the novel disabling means of the invention which here includes an O-ring sealed ("O") disabling plunger 105 having a stem portion 105a. When the disabling plunger 105 is deployed in the manner shown in FIG. 22A, stem 105a functions to block fluid flow through outlet passageway 110 (See FIG. 23) of the rate control assembly toward the administration set.

With the device in the configuration shown in FIG. 4 and with the fluid reservoir 65 filled with the medicament to be dispensed to the patient, the dispensing operation can be commenced by first removing the top cover 114 which has a circumferential protuberance 114a that is snapped over the circumferentially grooved upper housing (see FIGS. 4 and 4A). With the cover removed, the outer coil 87a of the administration line 82a of the administration set 82 as well as the inner coil thereof can be unwrapped from the downwardly protruding skirt 114a of cover 114 about which it has been coiled (see FIG. 4). Removal of the top cover 114 also exposes the rate control housing 94 and the penetrating member housing 84, which is biased upwardly by a biasing means, shown here as a biasing spring 116 that is supported between penetrating member housing 84 and connecter member 54 in the manner shown in FIG. 4.

Figure 20:
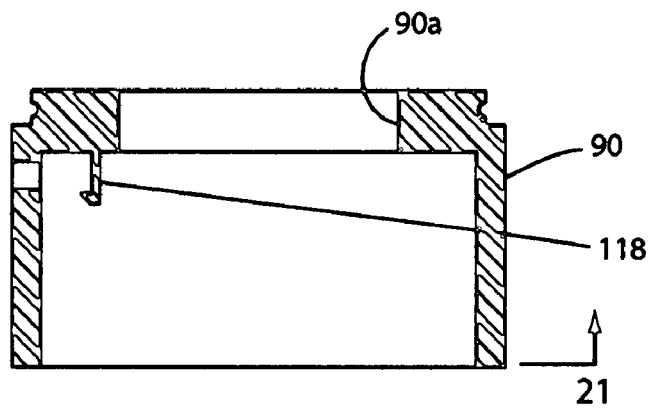
FIG. 20 is a cross-sectional view taken along lines 20-20 of FIG. 19.
Figure 21:
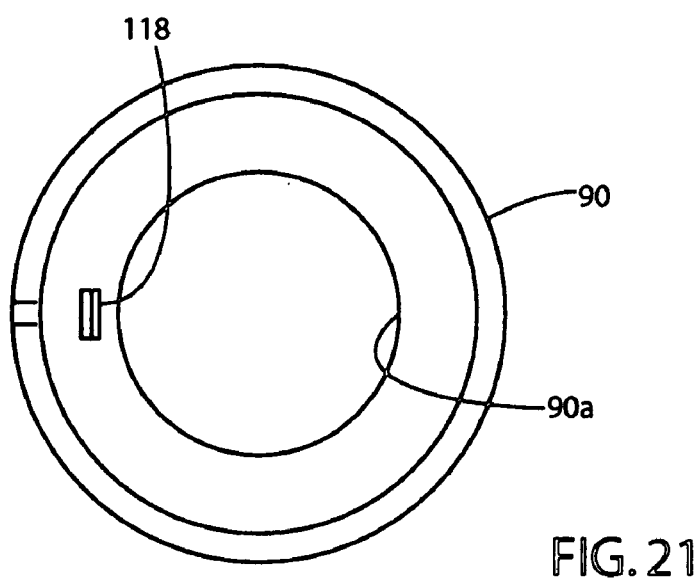
FIG. 21 is a view taken along lines 21-21 of FIG. 20.

Penetrating member housing 84 is locked against downward movement by the novel locking means of the invention, the operation of which is shown in FIGS. 29, 30 and 31. This important locking means, which prevents accidental dispensing of the medicinal fluid, here comprises a locking element 118 that forms a part of upper housing 90 (FIG. 20). Locking element 118 includes a yieldably deformable shank portion 118a and a locking tab portion 118b that normally engages a surface 120 formed on penetrating member housing 84 (FIGS. 4 and 14). Also forming a part of the locking means of the invention is a push button 122 that is carried by upper housing 90 and is movable within a push button cavity 124 formed in penetrating member housing 84 (FIGS. 14 and 29) from the first position shown in FIG. 29 into the second position shown in FIG. 30. Movement of the push button into the second position deforms the shank portion 118a of locking element 118 in the manner shown in FIG. 30 so that the locking tab portion 118b can freely pass through an opening 126 formed in penetrating member housing 84 (FIGS. 14 and 30). With this construction, a downward force exerted on the rate control housing 94 will cause downward movement of the penetrating member housing 84 against the urging of spring 116. As the penetrating member housing 84 moves from the first position shown in FIGS. 4 and 29 into the second position shown in FIGS. 4F and 31, the skirt portion 84a of housing 84 will move telescopically through the central opening 90a formed in upper housing 90. After movement of the penetrating member housing into the second position, the locking element 118 will return to its initial starting position as shown in FIG. 31.

Figure 15:
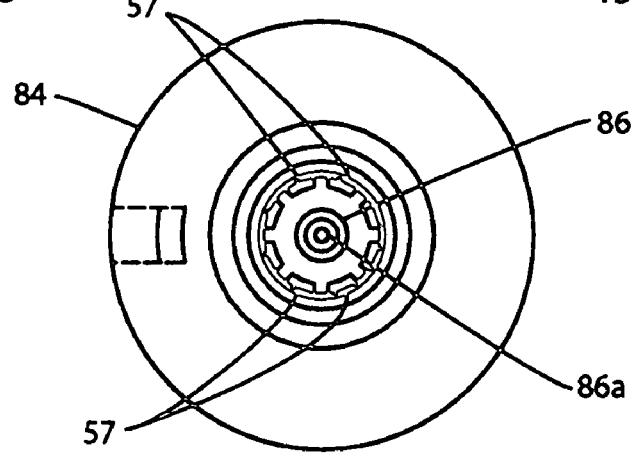
FIG. 15 is a view taken along lines 15-15 of FIG. 14.

During movement of the penetrating member housing into the second position, guide passageway 55a of the neck 55 of the connecter member 54 will closely guide the movement of the penetrating member toward the outlet 66 of the fluid reservoir 65. When the penetrating member housing reaches the second position shown in FIG. 33, locking tabs 57 formed on member 84 (FIG. 15) which has deformed inwardly and out of groove 55c will cooperate with a locking groove 55b (FIG. 11) to securely lock the connecter member in the second position.

Figure 11:
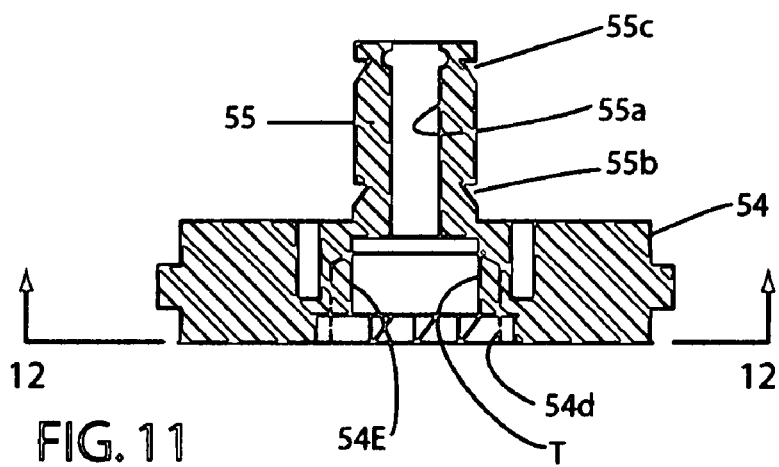
FIG. 11 is a cross-sectional view taken along lines 11-11 of FIG. 10.
Figure 12:
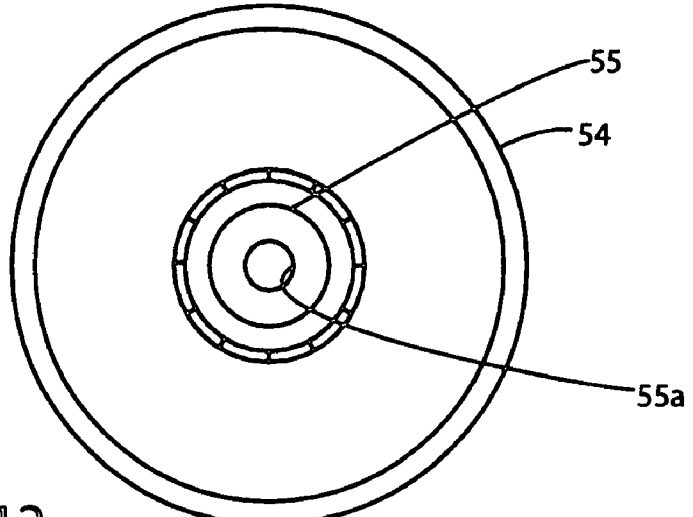
FIG. 12 is a view taken along lines 12-12 of FIG. 11.
Figure 13:
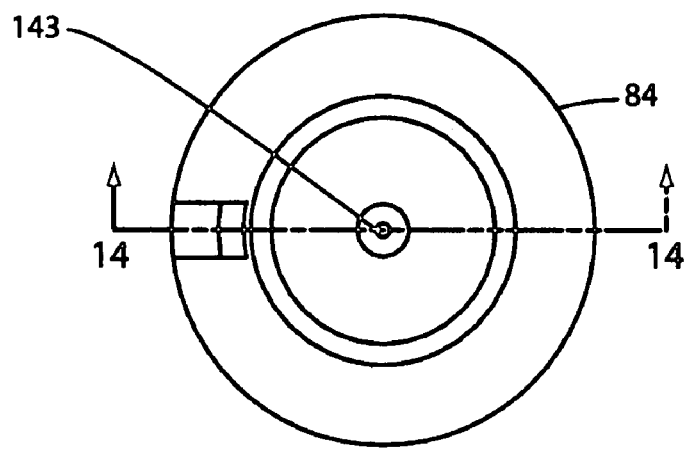
FIG. 13 is a top plan view of the penetrating member housing component of the device of the invention.

Downward movement of the rate control housing 94 and the penetrating member housing 84 will cause the penetrating member 86 having a sealing coating 84c to first pierce a septum membrane 128 (FIG. 44) that is superimposed over closure wall 68a and held in position by a cap 130 that is sealably connected to a flange 132 formed on neck portion 68 as by heat weldment. As shown in FIG. 4B, cap 130 is provided with a plurality of circumferentially spaced locking tabs 130a for holding the reservoir defining container in position within connector member 54. As shown in FIG. 11, connector member 54 also has a counterbore 54d that is provided with threads 54e for threadably receiving threaded cap 130.

After piercing septum membrane 128, the penetrating member will pierce closure wall 68a in the manner shown in FIGS. 4A and 4F. Piercing of the membrane 128 and the closure wall 68a opens a fluid communication path from reservoir 65 to the rate control assembly 94 via a central fluid passageway 86a formed in penetrating member 86 and a filter 135.

Figure 17:
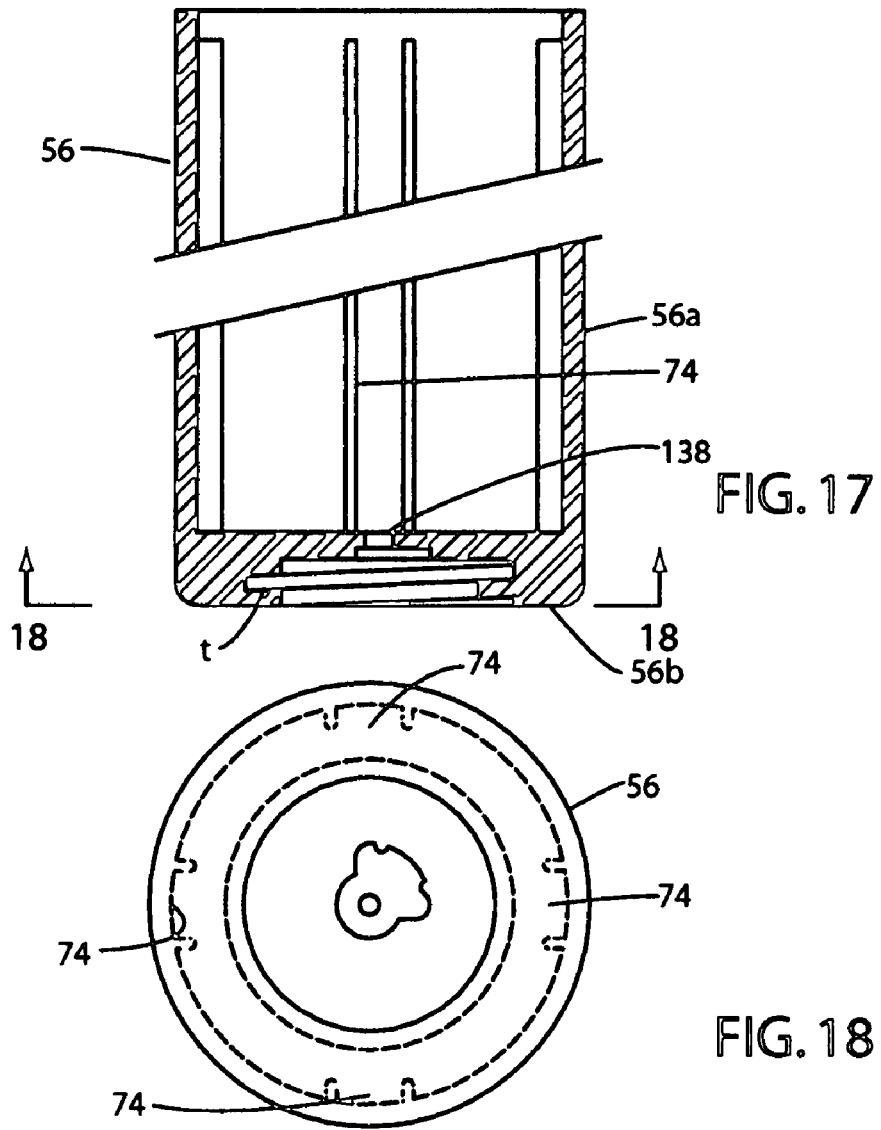
FIG. 17 is a cross-sectional view taken along lines 17-17 of FIG. 16.
Figure 18:
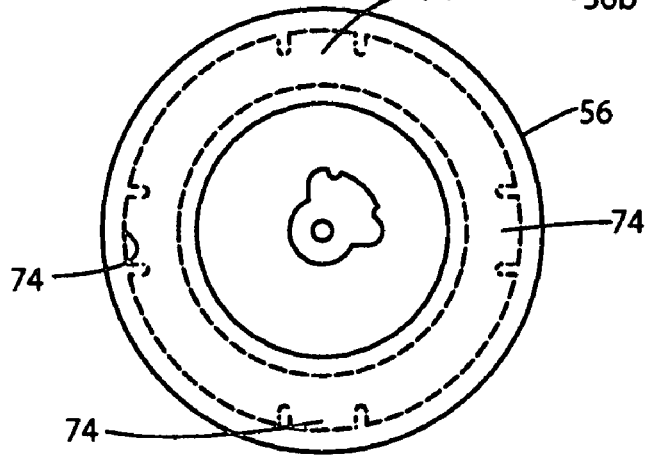
FIG. 18 is a view taken along lines 18-18 of FIG. 17.
Figure 19:
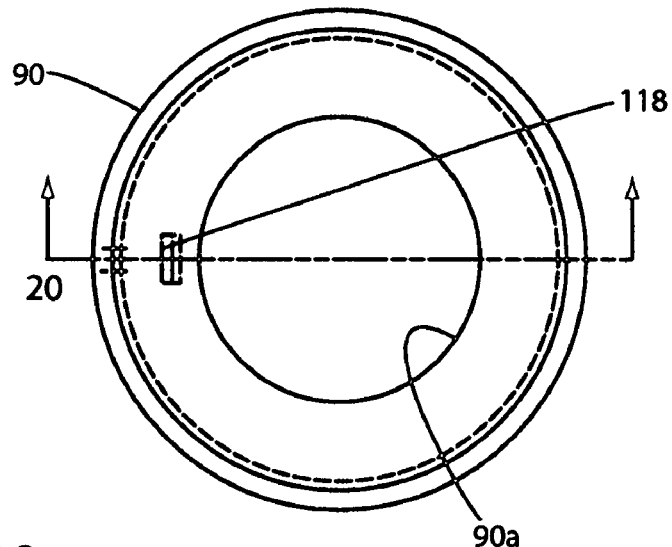
FIG. 19 is a top plan view of the upper dispenser housing component of the device of the invention.

Following manipulation of the carriage locking means of the invention in a manner to release the carriage 60 from base member 56b, spring 80 will move the carriage from the starting position shown in FIG. 4 to the extended position shown in FIG. 4A. In this regard, as best seen in FIGS. 4, 4F, 8 and 9, the carriage locking means includes a locking member 136 having a head portion 136a, and a shank portion 136b which extends through an opening 138 provided in the carriage base (see FIGS. 4F and 17) and a finger engaging operating portion 136c. Finger engaging operating portion 136c functions to rotate locking member 136 from the transverse locking position shown in FIG. 4 to a release position in alignment with keyhole opening 140 formed in carriage base 60a (FIGS. 4F and 9) to permit the release of the carriage assembly and to permit the stored energy means, or spring 80, to move the carriage from the starting position shown in FIG. 4 to the extended position shown in FIG. 4F.

As the carriage moves from the starting position to the extended position, the fluid will flow from reservoir 65, through central fluid passageway 86a of the penetrating member, through conventional particulate filter 135 carried by the penetrating member housing 86, through inlet 143 of member 84 (See FIG. 14), through inlet 145 of rate control cover 104 and into the inlet 106a of the rate control plate 100 (See FIG. 25 through 28). From inlet 106a, the fluid will flow into the circuitous fluid channel 106 formed in the rate control plate 100 (FIG. 25). Next the fluid will flow into outlet passageway 110 of rate control cover 102 and toward the administration set 82 via a passageway 94b formed in rate control housing 94 (FIGS. 4A, 22 and 23).

If at any time it is desired to disable the apparatus, disabling plunger 105 can be pushed inwardly causing stem portion 105a to block fluid flow through outlet passageway 110 of the rate control assembly toward the administration set.

Figures 33, 33B:
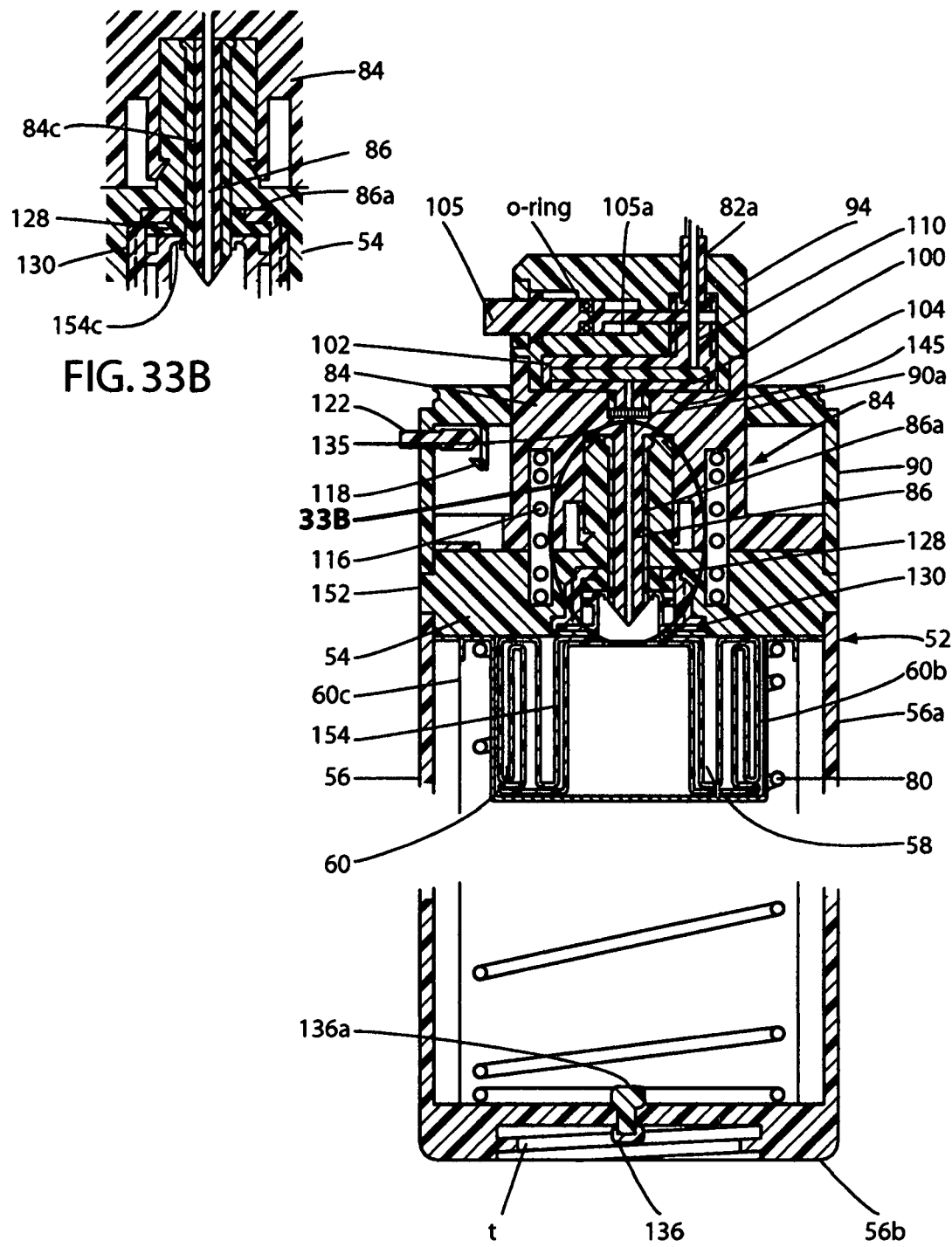
FIG. 33 is a longitudinal, cross-sectional view similar to FIG. 32, but showing the appearance of the device following the fluid dispensing step.
FIG. 33B is an enlarged, fragmentary, cross-sectional view of the area identified in FIG. 33 as 33B.

Referring next to FIGS. 32 and 33, yet another form of the dispensing device of the present invention for dispensing medicaments to a patient is there shown and generally designated by the numeral 152. This alternate form of dispensing apparatus is similar in most respects to that shown in FIGS. 1 through 31 and like numerals are used in FIGS. 32 and 33 to identify like components. The major difference between this latest embodiment of the invention and that shown in FIGS. 1 through 31 resides in the differently configured reservoir defining container 154.

As shown in FIGS. 32, 32B, 32C and 33, container 154, rather than being in the form of a container having a bellows-like sidewall, reservoir defining container 154 here comprises a semi-rigid collapsible container which is carried by a carriage assembly 58 which is of identical construction and operation to that previously described.

As best seen in FIG. 32C, collapsible container assembly 154 includes a collapsible sidewall 154a, an interconnected bottom wall 154b and an interconnected top wall 154c to which a sealed neck 154d is sealably interconnected. Collapsible container assembly 154 defines a fluid reservoir 157 having an inlet/outlet that is generally identified by the numeral 158. Collapsible sidewall 154a, bottom wall 154b and top wall 154c can be circular, oval or of other desired shapes.

As before, the dispensing device here includes a supporting structure 52, which includes a connector assembly 54 and a generally cylindrically shaped outer housing 56a that is interconnected with the connector member 54 in the manner best seen in FIG. 32 of the drawings.

Carriage assembly 58, which is movable between a first position shown in FIG. 32 and a second position shown in FIG. 33, is releasably locked in its first position by locking means that is also identical in construction and operation to the locking means previously described herein.

In the preferred form of this alternate embodiment of the invention, neck 154d is sealably interconnected with top wall 154c in accordance with an aseptic blow-fill seal technique of the general character previously described.

As in the earlier described form of the invention, an important feature of this latest form of the invention resides in the provision of novel guide means for guiding travel of carriage assembly 58 between the first position shown in FIG. 32 and the second position shown in FIG. 33. This important guide means is of identical construction and operation to that previously described herein.

To controllably move the carriage assembly from its first position to its second position, novel stored energy means are provided. This novel stored energy means, which is operably associated with carriage assembly 58, is here provided in the form of a coiled spring 80, which is also identical in construction and operation to that previously described.

As in the earlier described embodiment of the invention, when the locking means of the invention is manipulated in a manner to unlock the carriage assembly from base portion 56b of the outer housing, spring 80 will be allowed to move from its retracted position shown in FIG. 32 to its expanded position shown in FIG. 33 and in so doing will controllably move the carriage assembly from its starting position shown in FIG. 32 and, following operation of the reservoir accessing means, to its fully deployed or extended position shown in FIG. 33. As the carriage assembly moves toward its deployed position, the semi-rigid collapsible sidewall 154a of the collapsible container 154 will move into the collapsed configuration shown in FIG. 33. As the collapsible container collapses, the medicinal fluid contained within the container will be controllably expelled therefrom.

To further control the flow of medicinal fluid from the reservoir toward the administration set 82 of the invention and then on to the patient, flow control means are provided. This novel fluid flow control means, which is identical in construction and operation to that previously described, comprises two cooperating components, namely a rate control means for controlling the rate of fluid flow from the collapsible reservoir and a reservoir access means for controlling fluid flow between the collapsible reservoir and the rate control means. These important components are also identical in construction and operation to those described in the preceding paragraphs.

In operating the device of this latest form of the invention, with the fluid reservoir 157 filled with the medicament to be dispensed to the patient, the dispensing operation can be commenced by first removing the top cover 114 which is snapped over the upper housing. With top cover 114 removed, the administration line 82a of the administration set 82 can be unwrapped from the downwardly protruding skirt 114a of cover 114 about which it has been coiled (see FIG. 32). Removal of the top cover 114 also exposes the rate control housing 94 and the penetrating member housing 84 which is biased upwardly by biasing spring 116 that is supported between penetrating member housing 84 and connecter member 54.

As before, penetrating member housing 84 is locked against downward movement by the novel locking means of the invention, the operation of which is shown in FIGS. 29, 30 and 31. Following operation of the locking means, a downward force exerted on the rate control housing 94 will cause downward movement of the penetrating member housing 84 against the urging of spring 116. As the penetrating member housing 84 moves from the first position into the second position, the skirt portion of housing 84 will move telescopically through the central opening 90a formed in upper housing 90.

Downward movement of the rate control housing 94 and the penetrating member housing 84 will cause the penetrating member 86 to first pierce membrane 128 that is superimposed over closure wall 154c and secured in position by a cap 130 as by heat weldment. As shown in FIG. 32D, threaded cap 130 is provided with a plurality of circumferentially spaced locking tabs 130a for holding the reservoir defining container in position within connector member 154.

After piercing membrane 128, the penetrating member will pierce closure wall 154c in the manner shown in FIG. 33. Piercing of the membrane 128 and the closure wall opens a fluid communication path from reservoir 157 to the rate control assembly 94 via a central fluid passageway 86a formed in penetrating member 86 and filter 135.

Following manipulation of the carriage locking means of the invention in a manner to release the carriage 60 from the base member, spring 80 will move the carriage from the starting position shown in FIG. 32 to the extended position shown in FIG. 33.

As the carriage moves from the starting position to the extended position, the fluid will flow from reservoir 157, through central fluid passageway 86a of penetrating member, through conventional particulate filter 135 carried by penetrating member housing 84, through inlet 143 of member 84 (See FIG. 14), through inlet 145 of rate control cover 104 and into the inlet 106a of the rate control plate 100 (See FIG. 25 through 28). From inlet 106a, the fluid will flow into the circuitous fluid channel 106 formed in the rate control plate 100 (FIG. 25). Next the fluid will flow into outlet passageway 110 of rate control cover 102 and toward the administration set 82 via a passageway 94b formed in rate control housing 94 (FIGS. 4A, 22 and 23).

As before, if at any time it is desired to disable the apparatus, disabling plunger 105 can be pushed inwardly causing stem portion 105a to block fluid flow through outlet passageway 110 of the rate control assembly toward the administration set (See FIGS. 22, 23, 33 and 34).

Figure 34:
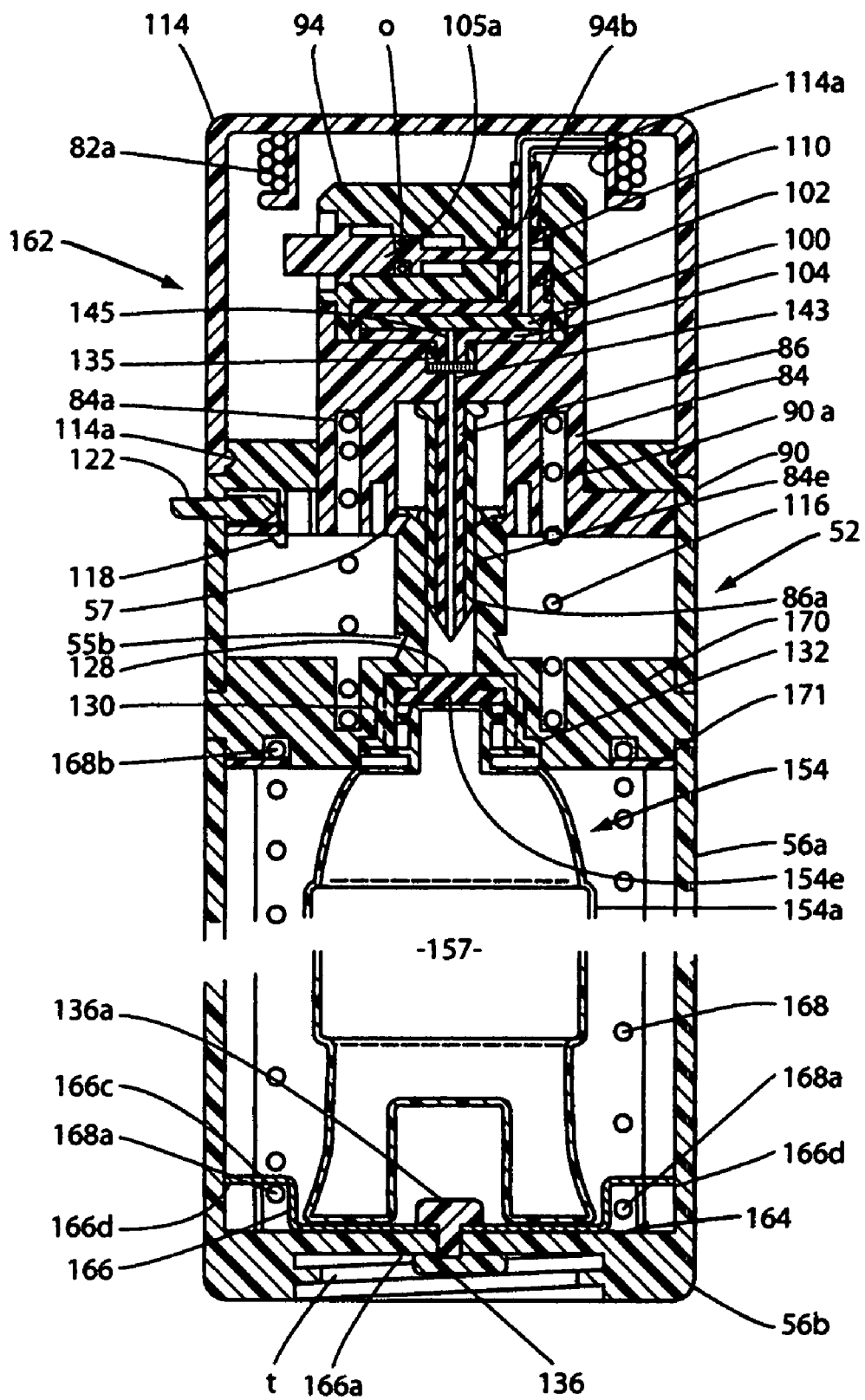
FIG. 34 is a longitudinal, cross-sectional view of still another form of the dispensing device of the invention illustrating a differently acting stored energy means.
Figure 35:
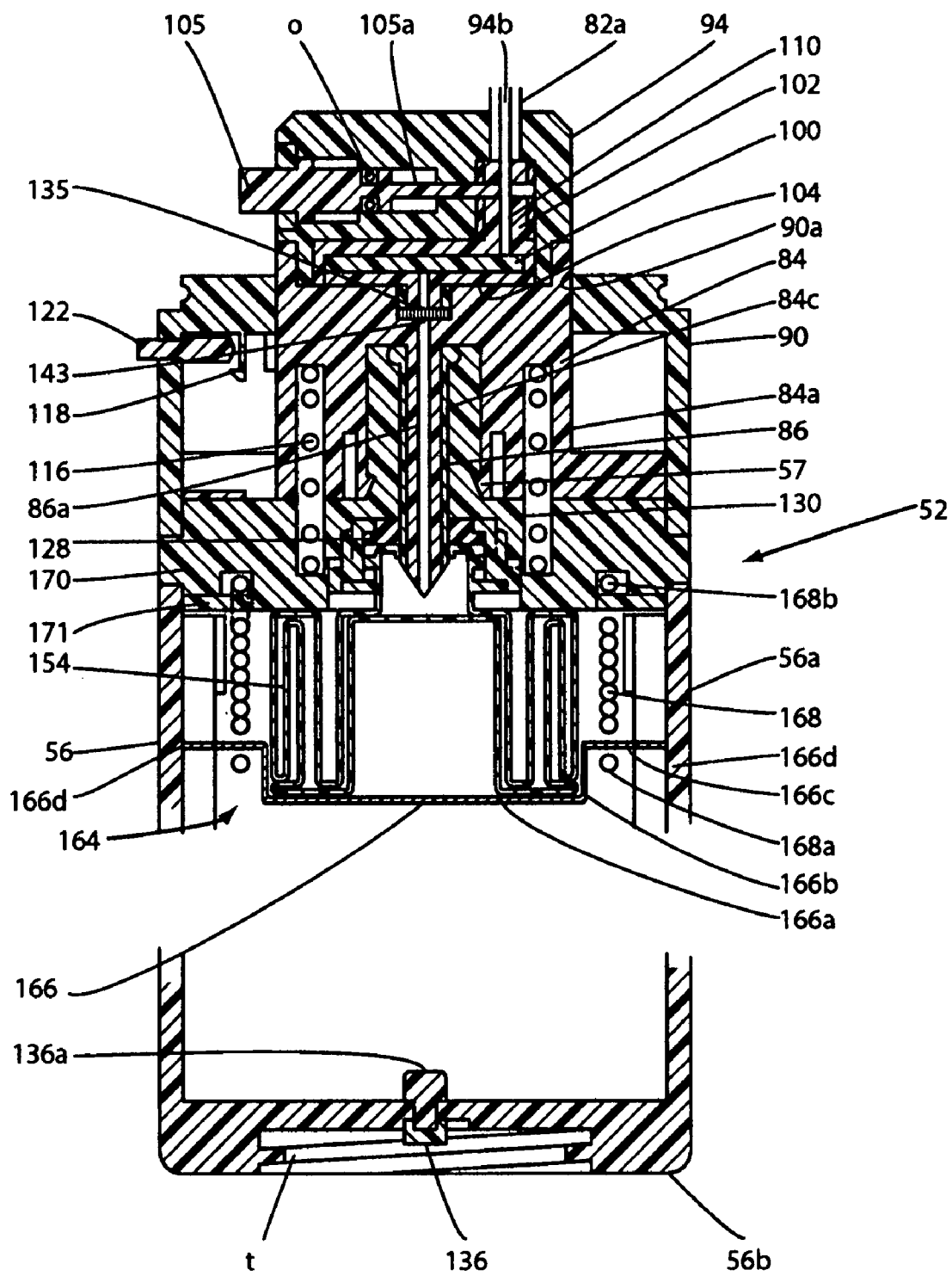
FIG. 35 is a longitudinal, cross-sectional view similar to FIG. 34 but showing the appearance of the device following the fluid dispensing step.

Referring next to FIGS. 34 and 35, still another form of the dispensing device of the present invention for dispensing medicaments to a patient is there shown and generally designated by the numeral 162. This alternate form of dispensing apparatus is similar in most respects to that shown in FIGS. 32 and 33 and like numerals are used in FIGS. 34 and 35 to identify like components. The major difference between this latest embodiment of the invention and that shown in FIGS. 32 and 33 resides in the manner in which the stored energy means operates to dispense the fluid from the fluid reservoir of the device.

As shown in FIGS. 34 and 35, reservoir defining container 154 is identical to that described in connection with the embodiment of FIG. 32 and is carried by a carriage assembly 164 which is of a slightly different construction from that previously described. More particularly, as shown in FIGS. 34, 34C and 34D, carriage assembly 164 comprises a carriage 166 having a carriage base 166a and a foreshortened, generally cylindrically shaped sidewall 166b which terminates in a radially outwardly and downwardly extending, hook-like flange 166c. As before, flange 166c includes a plurality of circumferentially spaced guide tabs 166d, the purpose of which will presently be described. Carriage assembly 166 is releasably locked in its first position by a locking means that is substantially identical in construction and operation to that previously described.

As before, the dispensing device here includes a supporting structure 52, which includes a slightly different connector assembly 170 and a generally cylindrically shaped outer housing 56a that is interconnected with the connector member 170 in the manner best seen in FIG. 32 of the drawings.

As in the earlier described embodiments of the invention, an important feature of this latest form of the invention resides in the provision of novel guide means for guiding travel of carriage assembly 164 between the first position shown in FIG. 34 and the second position shown in FIG. 35. This important guide means is of identical construction and operation to that previously described herein.

To controllably move the carriage assembly from its first position to its second position, a differently configured stored energy means is provided. This stored energy means, which is operably associated with carriage assembly 164, is here provided in the form of a coiled spring 168, which is initially extended and in tension (see FIG. 34). More particularly, as illustrated in FIG. 34, one end 168a of the coil spring 168 resides within the hook-like flange 166c and the other end 168b thereof is interconnected with the connector member 170 by means of a capture plate 171 (FIGS. 34 and 34A). With this construction, following operation of the reservoir accessing means, and when the locking means of the invention is manipulated in a manner to unlock the carriage assembly from base portion 56b of the main housing, spring 168, which is in tension, will move from its extended position as shown in FIG. 34 to its retracted position as shown in FIG. 35 and, in so doing, will controllably move the carriage assembly from its starting position shown in FIG. 34 to its fully deployed or extended position shown in FIG. 35.

As the carriage assembly moves toward its deployed position, the collapsible sidewall 154a of the semi-rigid collapsible container 154 will be collapsed and will move into the collapsed configuration shown in FIG. 35. As the collapsible container collapses, the medicinal fluid contained within the container will be controllably expelled therefrom.

To further control the flow of medicinal fluid from reservoir toward the administration set 82 of the invention and then on to the patient, flow control means are provided, which fluid flow control means, are identical in construction and operation to that previously described in the preceding paragraphs.

In operating the device of this latest form of the invention, with the fluid reservoir 157 filled with the medicament to be dispensed to the patient, the dispensing operation can be commenced by first removing the top cover 114 which is snapped over the upper housing and held in position by the circumferential protuberance 114a that is snapped over the circumferentially grooved upper housing. With top cover 114 removed, the administration line 82a of the administration set 82 can be unwrapped from the downwardly protruding skirt 114a of cover 114 about which it has been coiled (see FIG. 34). Removal of the top cover 114 also exposes the rate control housing 94 and the penetrating member housing 84 which is biased upwardly by biasing spring 116 that is supported between penetrating member housing 84 and connector member 170.

As before, penetrating member housing 84 is locked against downward movement by the novel initial locking means of the invention, the operation of which is shown in FIGS. 29, 30 and 31. Following operation of the locking means, a downward force exerted on the rate control housing 94 will cause downward movement of the penetrating member housing 84 against the urging of spring 116. As the penetrating member housing 84 moves from the first position into the second position, the skirt portion 84a of housing 84 will move telescopically through the central opening 90a formed in upper housing 90.

Downward movement of the rate control housing 94 and the penetrating member housing 84 will cause the penetrating member 86 to first pierce a septal membrane 128 that is superimposed over closure wall 154e and secured in position by cap 130 which is threadably secured within member 170. After piercing septal membrane 128, the penetrating member will pierce closure wall 154e in the manner shown in FIG. 35. Piercing of the membrane 128 and the closure wall opens a fluid communication path from reservoir 157 to the rate control assembly 94 via a central fluid passageway 86a formed in penetrating member 86 and filter 135.

Following manipulation of the carriage locking means of the invention in a manner to release the carriage 166 from the base member, spring 168 will move the carriage from the starting position shown in FIG. 34 to the retracted position shown in FIG. 35.

As the carriage moves from the starting position to the extended position, the fluid will flow from reservoir 157, through central fluid passageway 86a of penetrating member, through conventional particulate filter 135 carried by penetrating member housing 86, through inlet 143 of member 84 (See FIG. 14), through inlet 145 of rate control cover 104 and into the inlet 106a of the rate control plate 100 (See FIG. 25 through 28). From inlet 106a, the fluid will flow into the circuitous fluid channel 106 formed in the rate control plate 100 (FIG. 25). Next the fluid will flow into outlet passageway 110 of rate control cover 102 and toward the administration set 82 via a passageway 94b formed in rate control housing 94 (FIGS. 34 and 35).

As before, if at any time it is desired to disable the apparatus, disabling plunger 105 can be pushed inwardly causing stem portion 105a to block fluid flow through outlet passageway 110 of the rate control assembly toward the administration set.

Figure 36:
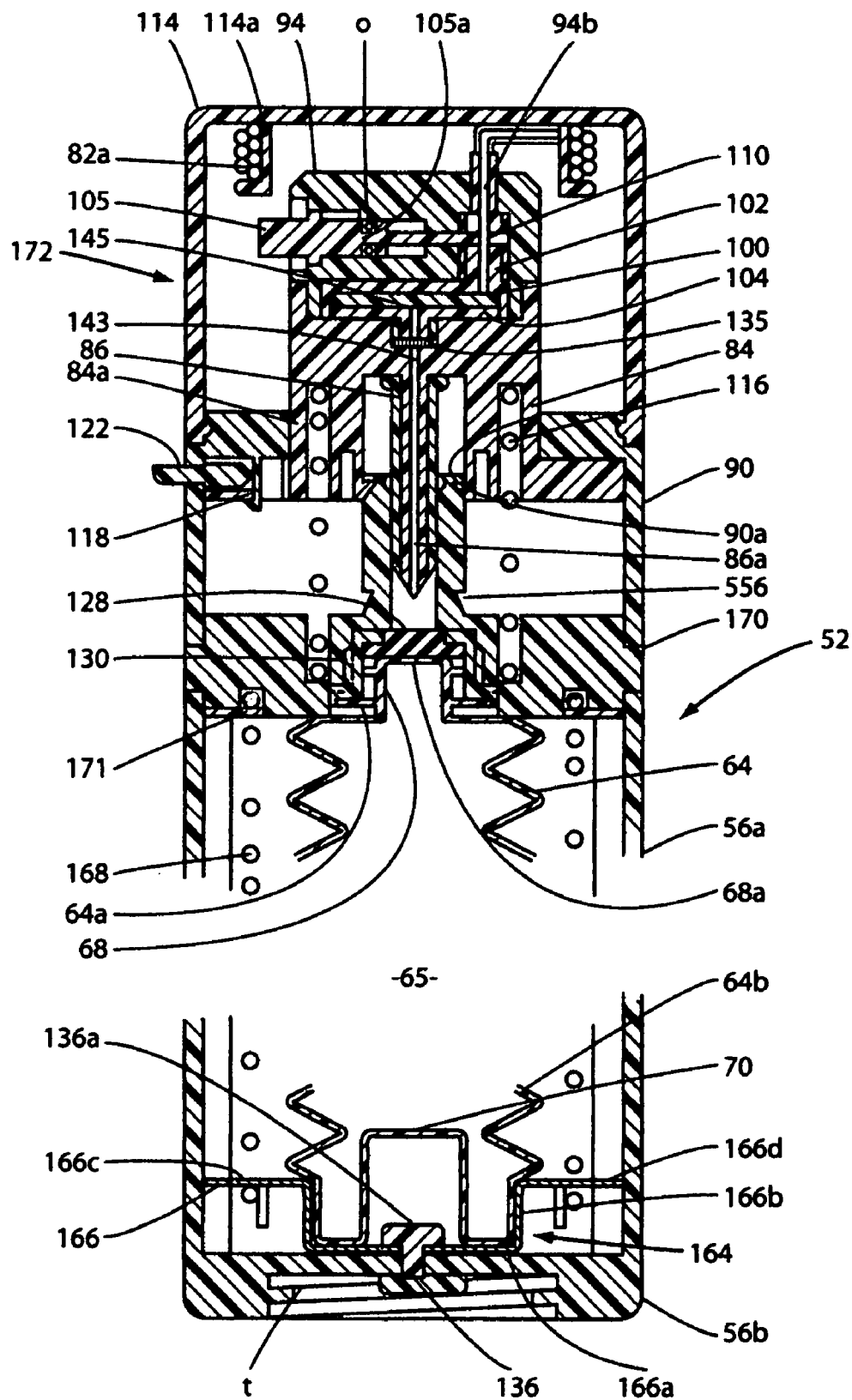
FIG. 36 is a longitudinal, cross-sectional view of yet another form of the dispensing device of the invention illustrating a different type of reservoir defining component.

Referring next to FIGS. 36 and 37, yet another form of the dispensing device of the present invention for dispensing medicaments to a patient is there shown and generally designated by the numeral 172. This alternate form of dispensing apparatus is similar in most respects to that shown in FIGS. 34 and 35 and like numerals are used in FIGS. 36 and 37 to identify like components. The major difference between this latest embodiment of the invention and that shown in FIGS. 34 and 35 resides in the differently configured fluid container. As shown in FIG. 36, the container, rather than being in the form of a semi-rigid collapsible container, such as container 154, here comprises a semi-rigid plastic container, similar to container 64 of the embodiment of the invention shown in FIGS. 1 through 31. As in the container 64 of the embodiment shown in FIGS. 1 through 31, the container illustrated in FIGS. 36 and 37 has a top wall 64a, a bellows-like sidewall 64b, a neck 68 and a bottom wall 70, which cooperate to define a fluid reservoir 65 that is connected to the connector member 170 in the manner previously described. Container 64 is carried by a carriage 166, which is of identical construction and operation to that previously described.

As before, the dispensing device here includes a supporting structure 52, which includes a connector member 170 and a generally cylindrically shaped outer housing 56a that is interconnected with the connector member 170 in the manner best seen in FIG. 36 of the drawings.

The guide means for guiding travel of carriage assembly 164 between the first position shown in FIG. 36 and the second position shown in FIG. 37 is of identical construction and operation to that previously described herein. Also of identical construction and operation to that previously described herein is the stored energy means which is operably associated with the carriage assembly 164.

As before, as the carriage assembly moves toward the deployed position shown in FIG. 37 due to the urging of tensioned spring 168, the sidewall 64b of container 64 will move into the collapsed configuration shown in FIG. 37. As the collapsible container collapses, the medicinal fluid contained within the container will be controllably expelled therefrom.

To further control the flow of medicinal fluid from reservoir toward the administration set 82 of the invention and then on to the patient, flow control means are provided which fluid flow control means are identical in construction and operation to that previously described in the preceding paragraphs.

In operating the device of this latest form of the invention, with the fluid reservoir 65 filled with the medicament to be dispensed to the patient, the dispensing operation can be commenced by first removing the top cover 114 which is snapped over the upper housing. With top cover 114 removed, the administration line 82a of the administration set 82 can be unwrapped from the downwardly protruding skirt 114a of cover 114 about which it has been coiled (see FIG. 36). Removal of the top cover 114 also exposes the rate control housing 94 and the penetrating member housing 84 which is biased upwardly by biasing spring 116 that is supported between penetrating member housing 84 and connecter member 170.

As before, penetrating member housing 84 is locked against downward movement by the novel locking means of the invention, the operation of which is shown in FIGS. 29, 30 and 31. Following operation of the locking means, a downward force exerted on the rate control housing 94 will cause downward movement of the penetrating member housing 84 against the urging of spring 116. As the penetrating member housing 84 moves from the first position into the second position, the skirt portion 84a of housing 84 will move telescopically through the central opening 90a formed in upper housing 90.

Downward movement of the rate control housing 94 and the penetrating member housing 84 will cause the penetrating member 86 to first pierce membrane 128 that is superimposed over closure wall 68a and held in position by cap 130. After piercing membrane 128, the penetrating member will pierce closure wall 68a in the manner shown in FIG. 37. Piercing of the membrane 128 and the closure wall opens a fluid communication path from reservoir 65 to the rate control assembly 94 via a central fluid passageway 86a formed in penetrating member 86 and filter 135.

Following manipulation of the carriage locking means of the invention in a manner to release the carriage 166 from the base member, spring 168 will move the carriage from the starting position shown in FIG. 36 to the retracted position shown in FIG. 37.

As the carriage moves from the starting position to the extended position, the fluid will flow from reservoir 65, through central fluid passageway 86a of penetrating member, through conventional particulate filter 135 carried by penetrating member housing 86, through inlet 143 of member 84 (See FIG. 14), through inlet 145 of rate control cover 104 and into the inlet 106a of the rate control plate 100 (See FIG. 25 through 28). From inlet 106a, the fluid will flow into the circuitous fluid channel 106 formed in the rate control plate 100 (FIG. 25). Next the fluid will flow into outlet passageway 110 of rate control cover 102 and toward the administration set 82 via a passageway 94b formed in rate control housing 94 (FIGS. 34 and 35).

As before, if at any time it is desired to disable the apparatus, disabling plunger 105 can be pushed inwardly causing stem portion 105a to block fluid flow through outlet passageway 110 of the rate control assembly toward the administration set.

Figures 38, 38A:
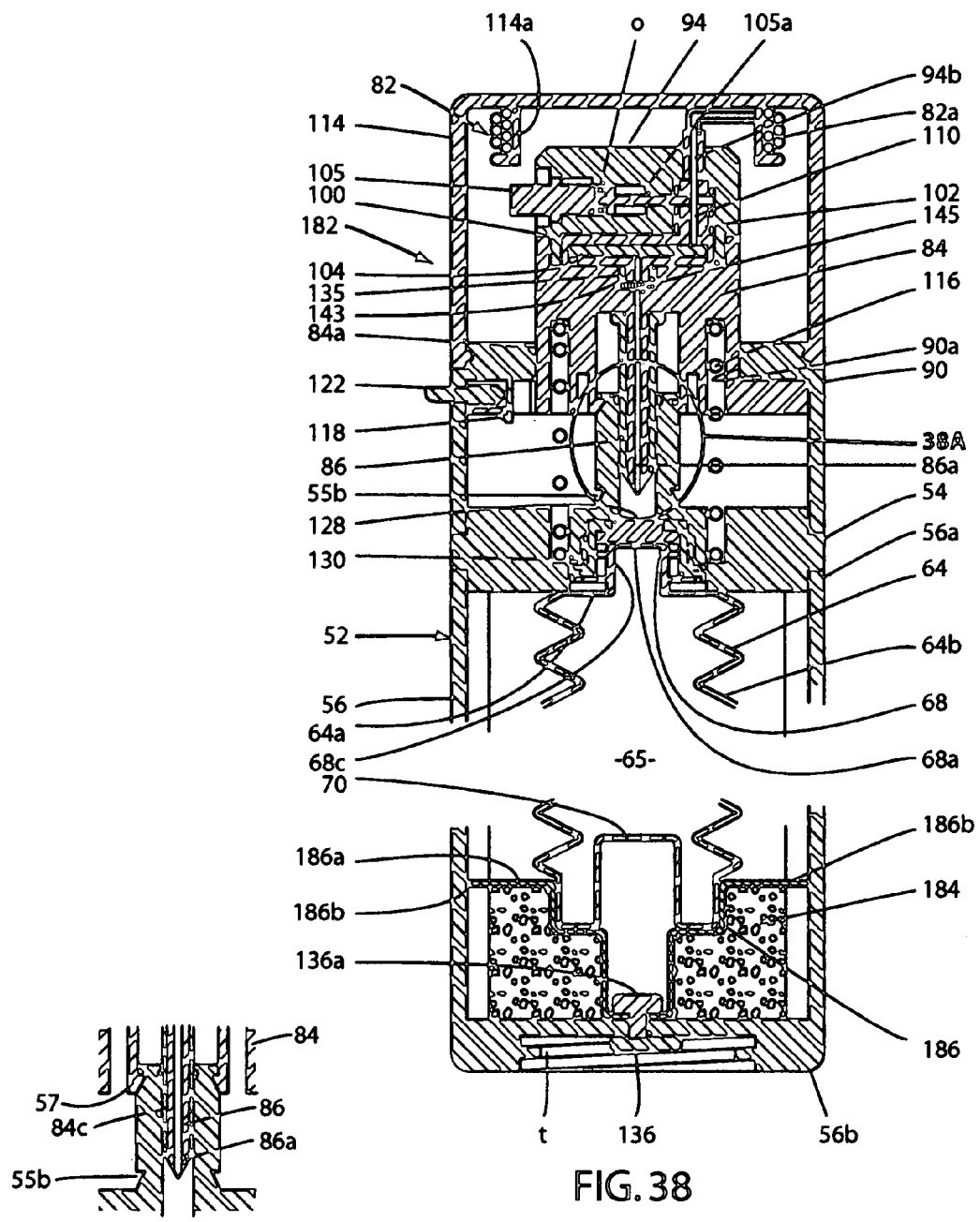
FIG. 38 is a longitudinal, cross-sectional view of another form of the dispensing device of the invention illustrating a totally different type of stored energy means.
FIG. 38A is an enlarged, fragmentary, cross-sectional view of the area designated in FIG. 38 as 38A.
Figures 39, 39A:
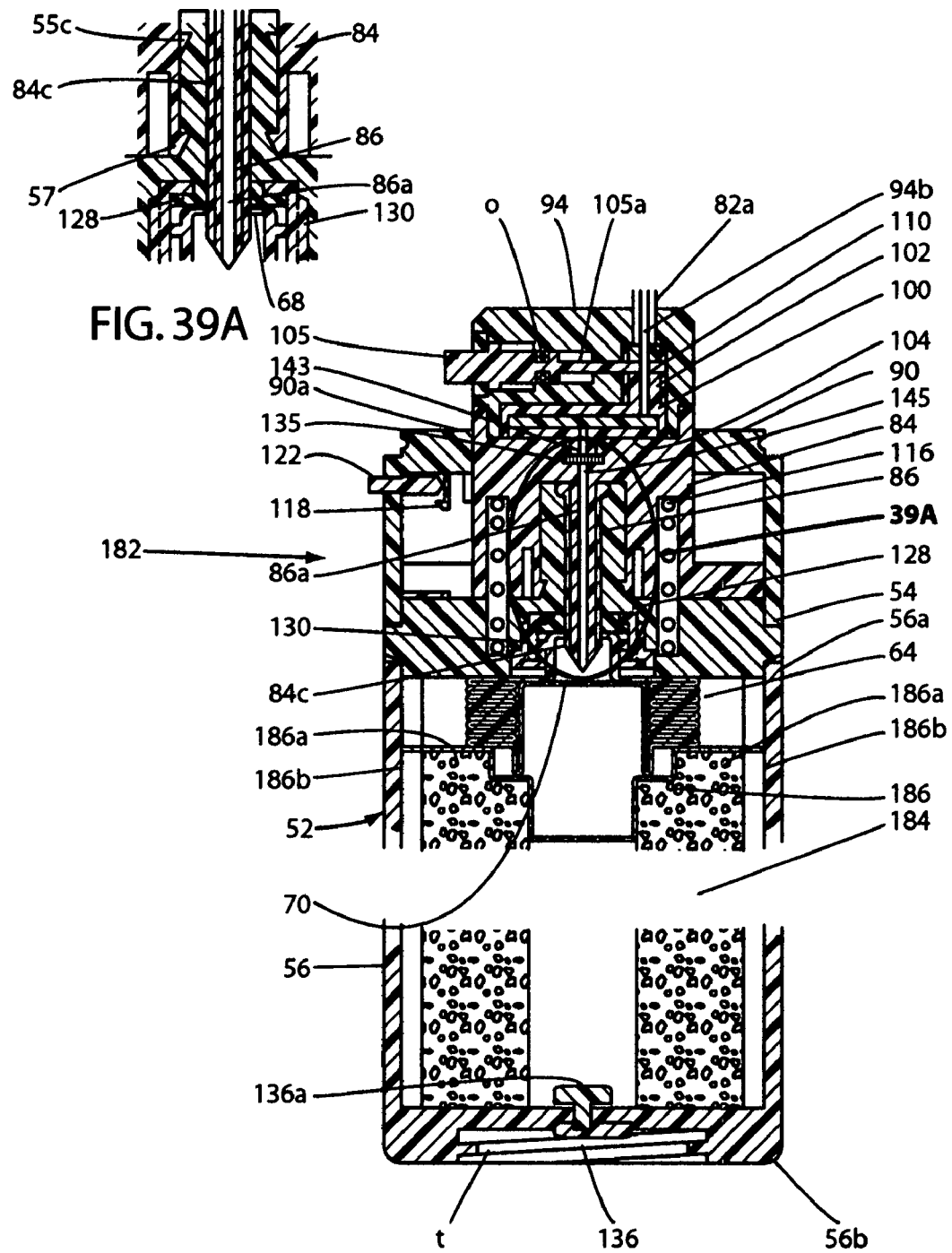
FIG. 39 is a longitudinal, cross-sectional view similar to FIG. 38 but showing the appearance of the device following the fluid dispensing step.
FIG. 39A is a fragmentary, cross-sectional view of the area designated in FIG. 39 as 39A.

Referring next to FIGS. 38 and 39, yet another form of the dispensing device of the present invention for dispensing medicaments to a patient is there shown and generally designated by the numeral 182. This alternate form of dispensing apparatus is similar in many respects to that shown in FIGS. 36 and 37 and like numerals are used in FIGS. 38 and 39 to identify like components. The major difference between this latest embodiment of the invention and that shown in FIGS. 36 and 37 resides in the totally different stored energy means for dispensing fluid from the fluid container.

More particularly, rather than being a mechanical spring, the novel stored energy means of this latest form of the invention comprises a compressible, expandable sponge-like configuration which is generally designated in the drawings by the numeral 184. This unique stored energy source, which functions to move the carriage from the first compressed position shown in FIG. 38 to the second expanded position shown in FIG. 39 can take several forms. By way of non-limiting example, stored energy source 184 can comprise a microporous, mesoporous, macroporous, ordered structure and can be constructed from silicone (SI), Polypropylene (PP), Ultra High Molecular Weight Polyethylene (UHMWPE), High Density Polyethylene (HDPE), Polyvinylidene Fluoride (PVDF), Ethyle-vinyl Acetate (EVA), Styrene Acrylonitrile (SAN), Polytetrafluroethylene (PTFE) and porous cellulose acetate. However, practice has shown that any porous plastic material including an open cell, porous foam or sponge-like material is suitable for use in constructing the stored energy source. The stored energy material employed may also be a cellular metal, a porous metal, a metal sponge or a solid metal foam. The metal foams may be derived from a single element or alloys of two or more elements. The metals or alloys comprising the foams may be crystalline or amorphous. They may also have regions that display semi-crystalline characteristics. General examples of these materials include Al, Cu/Al, Sn, Au, Pb, brass, steel and negative Poisson metal foams.

Figure 38B:
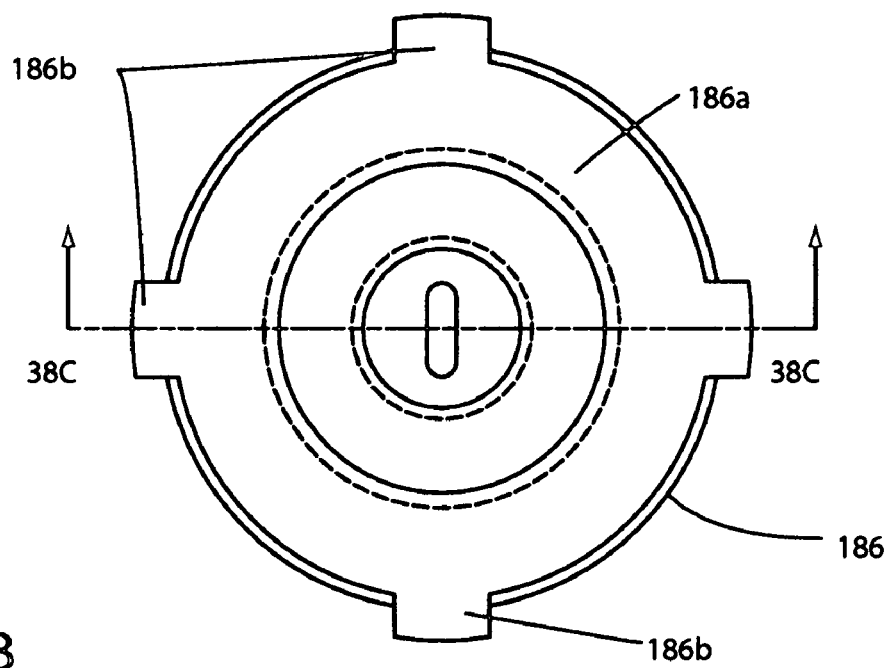
FIG. 38B is a top plan view of the carriage of this latest form of the invention.
Figure 38C:
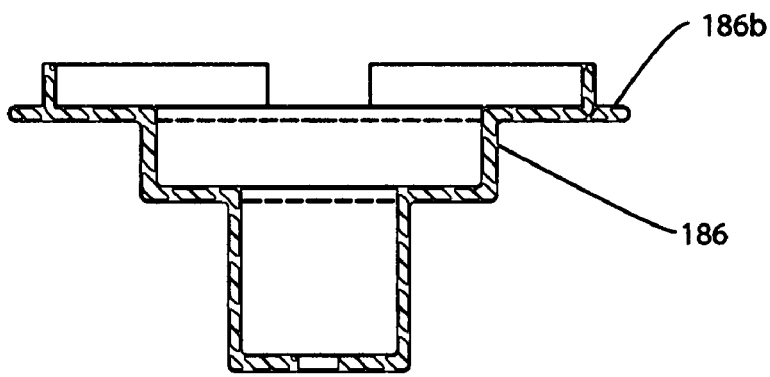
FIG. 38C is a cross-sectional view taken along lines 38C-38C of FIG. 38B.

As shown in FIG. 38, the container is similar in construction to the container 64 of the embodiment shown in FIGS. 1 through 31 and has a top wall 64a, a bellows-like sidewall 64b, a neck 68c and a bottom wall 70, which cooperate with sidewall 64b to define a fluid reservoir 65 that is suitably connected as by threaded engagement to connector member 54. Container 64 is carried by a carriage 186, which is of a somewhat similar construction to that previously described and includes a flange 186a and guide tabs or ears 186b (see FIGS. 38B and 38C).

As before, the dispensing device here includes a supporting structure 52 which includes a connector assembly 54, which is similar to that shown in FIG. 4, and a generally cylindrically shaped outer housing 56a that is interconnected with the connector member 54 in the manner best seen in FIG. 38 of the drawings.

The guide means for guiding travel of carriage 186 between the first position shown in FIG. 38 and the second position shown in FIG. 39 is of identical construction and operation to that previously described herein. Also of identical construction and operation to that previously described herein is the carriage locking means of the invention, which is operably associated with the carriage assembly.

As before, as the carriage assembly moves toward the deployed position shown in FIG. 39 due to the urging of the expanding cellular member, or sponge, 184, the sidewall 64b of container 64 will move into the collapsed configuration shown in FIG. 39. As the collapsible container collapses, the medicinal fluid contained within the container will be controllably expelled therefrom.

To further control the flow of medicinal fluid from the reservoir toward the administration set 82 of the invention and then on to the patient, flow control means are provided, which fluid flow control means are identical in construction and operation to that previously described in the preceding paragraphs.

In operating the device of this latest form of the invention, with the fluid reservoir 65 filled with the medicament to be dispensed to the patient, the dispensing operation can be commenced by first removing the top cover 114 which is snapped over the upper housing. With top cover 114 removed, the administration line 82a of the administration set 82 can be unwrapped from the downwardly protruding skirt 114a of cover 114 about which it has been coiled (see FIG. 38). Removal of the top cover 114 also exposes the rate control housing 94 and the penetrating member housing 84, which is biased upwardly by biasing spring 116 that is supported between penetrating member housing 84 and connecter member 54.

As before, penetrating member housing 84 is locked against downward movement by the novel locking means of the invention, the operation of which is shown in FIGS. 29, 30 and 31. Following operation of the locking means, a downward force exerted on the rate control housing 94 will cause downward movement of the penetrating member housing 84 against the urging of spring 116. As the penetrating member housing 84 moves from the first position into the second position, the skirt portion 84a of housing 84 will move telescopically through the central opening 90a formed in upper housing 90.

Downward movement of the rate control housing 94 and the penetrating member housing 84 will cause the penetrating member 86 to first pierce membrane 128 that is superimposed over closure wall 68a and secured in position, as by heat welding cap 130. After piercing membrane 128, the penetrating member will pierce closure wall 68a in the manner shown in FIG. 39. Piercing of the membrane 128 and the closure wall opens a fluid communication path from reservoir 65 to the rate control assembly 94 via central fluid passageway 86a formed in penetrating member 86 and filter 135.

Following manipulation of the carriage locking means of the invention in a manner to release the carriage 186 from the base member, sponge 184 will move the carriage from the starting position shown in FIG. 38 to the extended position shown in FIG. 39.

As the carriage moves from the starting position to the extended position, the fluid will flow from reservoir 65, through central fluid passageway 86a of the penetrating member, through conventional particulate filter 135 which is carried by penetrating member housing 86, through inlet 145 of member 84 (See FIG. 14), through inlet 145 of rate control cover 104 and into the inlet 106a of the rate control plate 100 (See FIG. 25 through 28). From inlet 106a, the fluid will flow into the circuitous fluid channel 106 formed in the rate control plate 100 (FIG. 25). Next the fluid will flow into outlet passageway 110 of rate control cover 102 and toward the administration set 82 via a passageway 94b formed in rate control housing 94.

As before, if at any time it is desired to disable the apparatus, disabling plunger 105 can be pushed inwardly causing stem portion 105a to block fluid flow through outlet passageway 110 of the rate control assembly toward the administration set.

Figures 40, 40A:
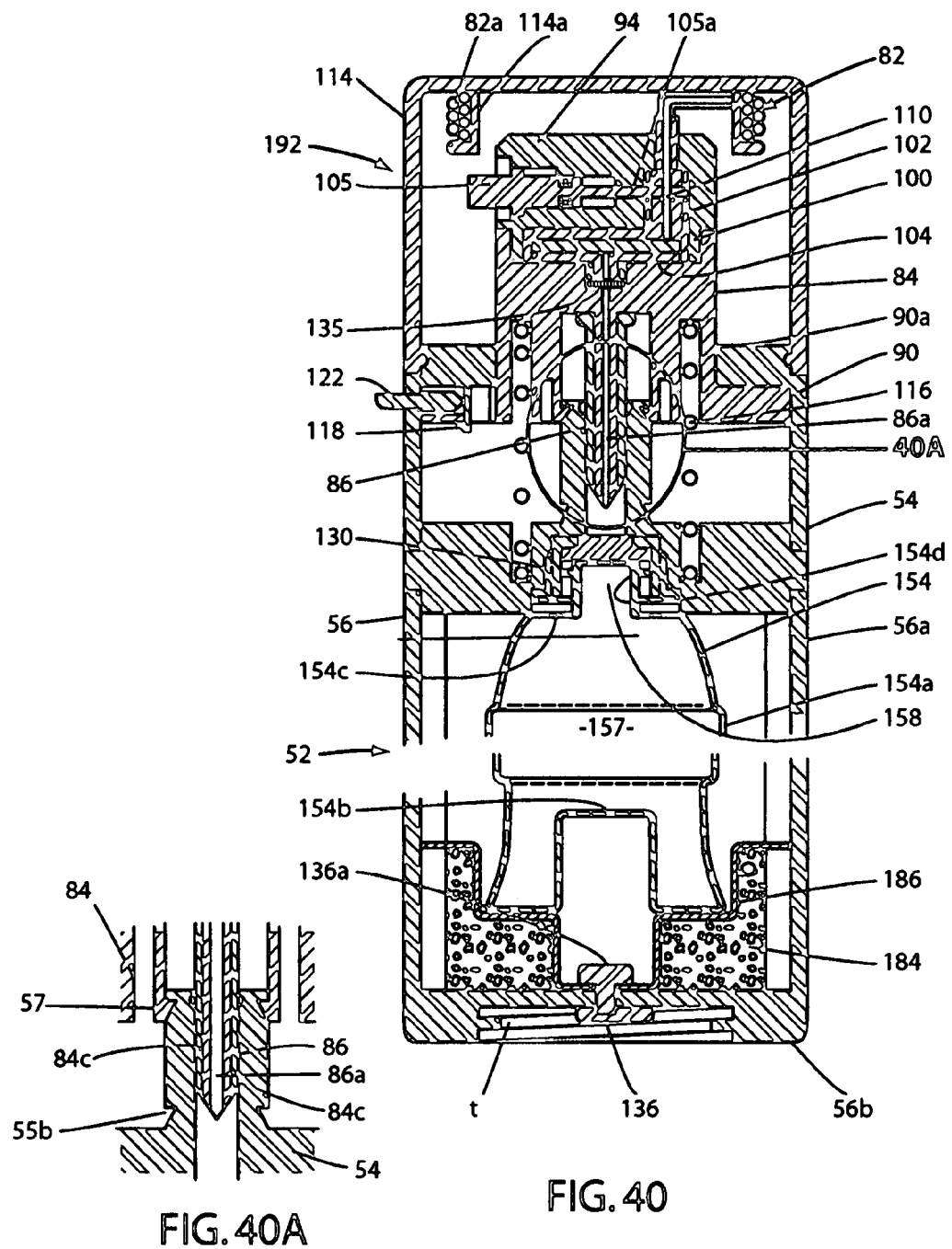
FIG. 40 is a longitudinal, cross-sectional view of still another form of the dispensing device of the invention illustrating a different type of reservoir defining component.
FIG. 40A is an enlarged, fragmentary, cross-sectional view of the area designated as 40A in FIG. 40.
Figures 41, 41A:
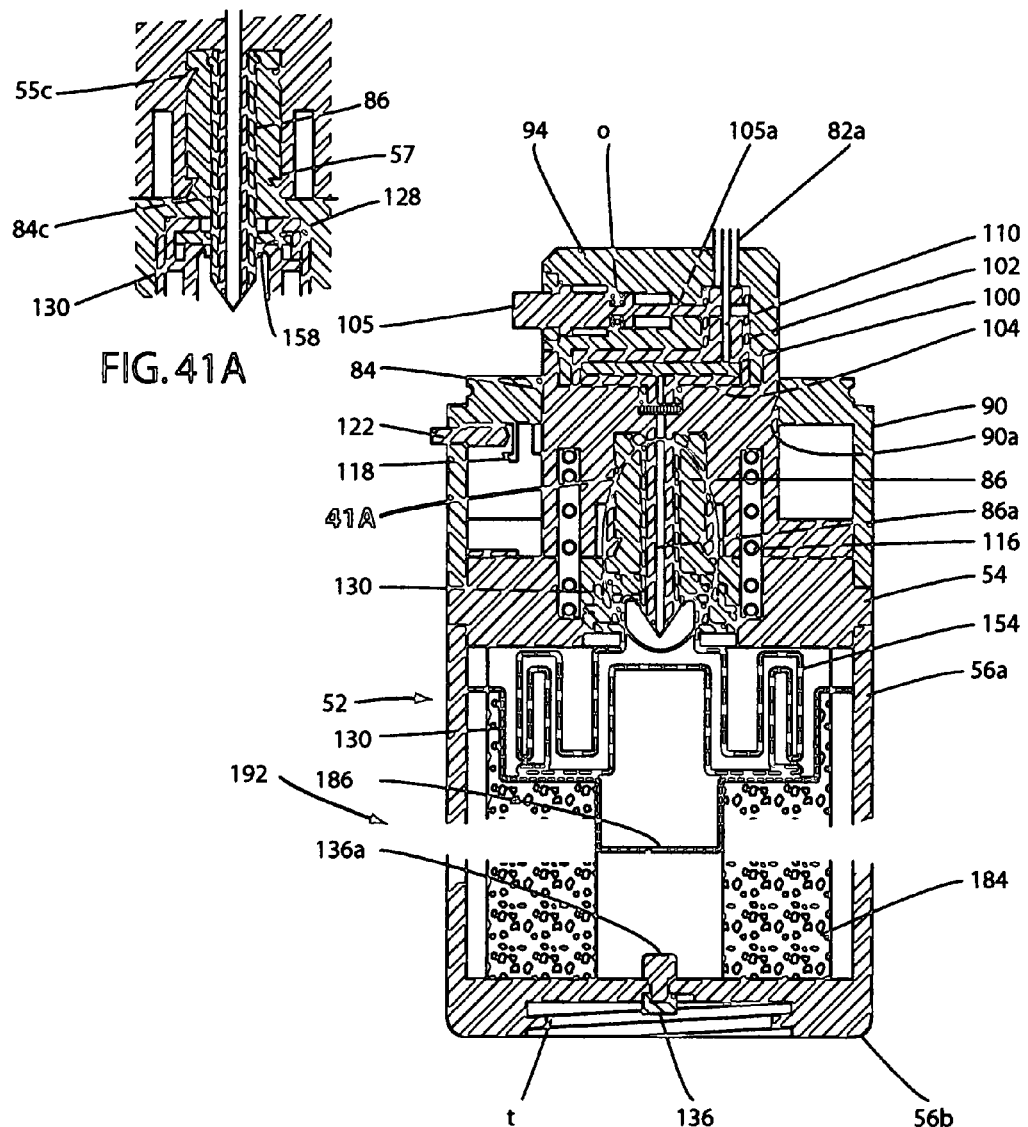
FIG. 41 is a longitudinal, cross-sectional view similar to FIG. 40, but showing the appearance of the device following the fluid dispensing step.
FIG. 41A is an enlarged, fragmentary, cross-sectional view of the area designated as 41A in FIG. 41.

Referring next to FIGS. 40 and 41, still another form of the dispensing device of the present invention for dispensing medicaments to a patient is there shown and generally designated by the numeral 192. This alternate form of dispensing apparatus is similar in many respects to that shown in FIGS. 38 and 39 and like numerals are used in FIGS. 40 and 41 to identify like components. The major difference between this latest embodiment of the invention and that shown in FIGS. 38 and 39 resides in the differently configured reservoir defining container 154, which is similar to that shown in FIG. 32.

As shown in FIGS. 40 and 41, container 154, rather than being in the form of a container having a bellows-like sidewall, reservoir defining container 154 here comprises a semi-rigid collapsible container which is carried by a carriage assembly 186 which is of identical construction and operation to that described in connection with the embodiment of FIGS. 38 and 39. More particularly, collapsible container assembly 154 includes a collapsible sidewall 154a, an interconnected bottom wall 154b and an interconnected top wall 154c to which a sealed neck 154d is interconnected. Collapsible container assembly 154 defines a fluid reservoir 157 having an inlet/outlet that is generally identified by the numeral 158.

The novel stored energy means of this latest form of the invention is identical in construction and operation to that described in connection with the embodiment of FIGS. 38 and 39 and comprises a compressible, expandable sponge-like configuration which is generally designated in the drawings by the numeral 184. As before, this unique stored energy source functions to move the carriage from the first compressed position shown in FIG. 40 to the second expanded position shown in FIG. 41.

As before, the dispensing device here includes a supporting structure 52 which includes a connector assembly 54, which is similar to that shown in FIG. 4, and a generally cylindrically shaped outer housing 56a that is interconnected with the connector member 54 in the manner best seen in FIG. 40 of the drawings.

The guide means for guiding travel of carriage 186 between the first position shown in FIG. 40 and the second position shown in FIG. 41 is of identical construction and operation to that previously described herein. Also of identical construction and operation to that previously described herein is the carriage locking means of the invention which is operably associated with the carriage assembly.

As before, as the carriage assembly moves toward the deployed position shown in FIG. 41 due to the urging of the expanding cellular member, or sponge, 184, the sidewall 154a of container will move into the collapsed configuration shown in FIG. 41. As the collapsible container collapses, the medicinal fluid contained within the container will be controllably expelled therefrom.

To further control the flow of medicinal fluid from the reservoir toward the administration set 82 of the invention and then on to the patient, flow control means are provided, which fluid flow control means, are identical in construction and operation to that previously described in the preceding paragraphs.

Operation of the device of this latest form of the invention is identical to that described in connection with the embodiment of FIGS. 38 and 39.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A dispensing device for dispensing medicaments to a patient comprising:
    (a) a supporting structure comprising a base assembly and a generally cylindrically shaped outer housing interconnected with said base assembly;
    (b) a carriage assembly interconnected with said supporting structure for movement between a first position and a second position, said carriage assembly comprising a carriage having a carriage base provided with a plurality of circumferentially spaced openings and a generally cylindrically shaped sidewall terminating in a radially outwardly extending flange;
    (c) locking means carried by said supporting structure for locking said carriage assembly in said first position;
    (d) a collapsible reservoir carried by said carriage assembly for containing fluid to be dispensed to the patient, said collapsible reservoir having an outlet port and comprising a blow-molded, collapsible container having a collapsible side wall, a bottom wall connected to said collapsible side wall, said bottom wall having an upstanding ullage portion, a top wall connected to said collapsible side wall and a reservoir septum assembly sealably connected to said top wall, said reservoir septum assembly including a pierceable septum;
    (e) a stored energy means operably associated with said carriage assembly for moving said carriage assembly between said first and second positions, said stored energy means comprising a coil spring having a first end in engagement with said supporting structure and a second end in engagement with said radially outwardly extending flange of said carriage;
    (f) an administration set, including an administration line interconnected with said outlet port of said collapsible reservoir; and
    (g) fluid flow control means carried by said base assembly of said supporting structure for controlling fluid flow from said collapsible reservoir toward said administration set, said fluid flow control means being movable from a first position to a second position and comprising:
        (i) rate control means carried by said supporting structure for controlling the rate of fluid flow from said collapsible reservoir toward said administration set, said rate control means comprising a rate control plate having a fluid flow micro-channel interconnected with said outlet of said collapsible reservoir; and
        (ii) reservoir accessing means for controlling fluid flow between said collapsible reservoir and said rate control means, said reservoir accessing means comprising a septum penetrating member for penetrating said pierceable septum of said reservoir septum assembly of said blow-molded, collapsible container.

2. The dispensing device as defined in claim 1, further including disabling means carried by said supporting structure for blocking fluid flow toward said administration set.

3. The dispensing device as defined in claim 1 in which said collapsible reservoir comprises a bellows structure.

4. The dispensing device as defined in claim 1 in which said collapsible reservoir is semi-rigid.

5. The dispensing device as defined in claim 1 in which said collapsible reservoir is constructed from a plastic material.

6. The dispensing device as defined in claim 1 in which said collapsible reservoir is pre-filled with the fluid to be dispensed to the patient.

7. The dispensing device as defined in claim 1 in which said collapsible reservoir is pre-filled with an injectable medicament.

8. The dispensing device as defined in claim 1 in which said collapsible reservoir is pre-filled with a parental fluid.

9. A dispensing device for dispensing medicaments to a patient comprising:
   (a) a supporting structure;
   (b) a reservoir defining assembly that defines a collapsible reservoir carried by said supporting structure, said collapsible reservoir being constructed from a single extrudable plastic parison as a prefilled container containing fluid and having an outlet port, said reservoir defining assembly comprising:
      (i) a neck portion having a closure wall,
      (ii) a side wall connected to said neck portion,
      (iii) a bottom wall connected to said side wall, said bottom wall including an upstanding ullage portion;
      (iv) a septum membrane superimposed over said closure wall; and
      (v) a cap connected to said neck portion for holding said septum membrane in position;
   (c) a coil spring operably associated with said collapsible reservoir for collapsing said reservoir;
   (d) an administration set, including an administration line interconnected with said outlet port of said collapsible reservoir;
   (e) fluid flow control means carried by said supporting structure for controlling fluid flow from said collapsible reservoir toward said administration set, said fluid flow control means being movable from a first position to a second position and comprising:
      (i) rate control means for controlling the rate of fluid flow from said collapsible reservoir toward said administration set, said rate control means comprising a rate control plate having a circuitous fluid flow micro-channel formed therein; and
      (ii) reservoir accessing means for controlling fluid flow between said collapsible reservoir and said rate control means.

10. The dispensing device as defined in claim 9 in which said reservoir accessing means comprises a penetrating member for penetrating said closure wall of said neck portion of said reservoir defining assembly and for penetrating said septum membrane of said reservoir defining assembly.

11. A dispensing device for dispensing medicaments to a patient comprising:
   (a) a supporting structure comprising a base assembly and a housing interconnected with said base assembly;
   (b) a carriage assembly interconnected with said supporting structure for movement between a first position and a second position;
   (c) a reservoir defining assembly that defines a semi-rigid collapsible reservoir carried by said carriage assembly, said semi-rigid collapsible reservoir being constructed from a single extrudable plastic parison as a prefilled container containing fluid to be dispensed to the patient, said collapsible reservoir having an outlet port and comprising a neck portion having a closure wall, a side wall connected to said neck portion and a bottom wall connected to said side wall, said bottom wall including an upstanding ullage portion and a slit septum closing said outlet port of said collapsible reservoir;
   (d) guide means connected to said supporting structure for guiding travel of said carriage assembly between said first position and said second position, said guide means comprising a guide member connected to said base assembly and a guide rib connected to said housing of said supporting structure;
   (e) a stored energy means operably associated with said carriage assembly for moving said carriage assembly between said first and second positions, said stored energy means comprising a spring;
   (f) an administration set, including an administration line interconnected with said outlet port of said collapsible reservoir;
   (g) fluid flow control means carried by said base assembly of said supporting structure for controlling fluid flow from said collapsible reservoir toward said administration set, said fluid flow control means being movable from a first position to a second position and comprising a reservoir accessing a means, including a blunt-ended penetrating member.

\* \* \* \* \*